(12) United States Patent
Rajagopal et al.

(10) Patent No.: US 10,081,844 B2
(45) Date of Patent: Sep. 25, 2018

(54) CHROMOPHORE-BASED PCR METHODS FOR DETECTING AND CHARACTERIZING NUCLEIC ACIDS IN SAMPLES

(71) Applicant: California Institute of Technology, Pasadena, CA (US)

(72) Inventors: Aditya Rajagopal, Irvine, CA (US); Mark D. Goldberg, Alta Loma, CA (US); Erika F. Garcia, Los Angeles, CA (US); Xiomara L. Madero, Glendale, CA (US); Thomas A. Tombrello, Altadena, CA (US); Axel Scherer, Barnard, VT (US)

(73) Assignee: California Institute of Technology, Pasadena, CA (US)

(*) Notice: Subject to any disclaimer, the term of this patent is extended or adjusted under 35 U.S.C. 154(b) by 0 days.

(21) Appl. No.: 15/675,048

(22) Filed: Aug. 11, 2017

(65) Prior Publication Data
US 2018/0030551 A1   Feb. 1, 2018

Related U.S. Application Data

(63) Continuation of application No. 14/162,725, filed on Jan. 23, 2014, now abandoned.

(60) Provisional application No. 61/756,343, filed on Jan. 24, 2013.

(51) Int. Cl.
| | |
|---|---|
| *C12P 19/34* | (2006.01) |
| *C12Q 1/70* | (2006.01) |
| *C12Q 1/6851* | (2018.01) |
| *C12Q 1/68* | (2018.01) |

(52) U.S. Cl.
CPC ............. *C12Q 1/701* (2013.01); *C12Q 1/68* (2013.01); *C12Q 1/6851* (2013.01); *C12Q 1/703* (2013.01); *Y10T 436/143333* (2015.01)

(58) Field of Classification Search
None
See application file for complete search history.

(56) References Cited

U.S. PATENT DOCUMENTS

| | | |
|---|---|---|
| 3,996,345 A | 12/1976 | Ullman et al. |
| 4,351,760 A | 9/1982 | Khanna et al. |
| 4,683,195 A | 7/1987 | Mullis et al. |
| 4,683,202 A | 7/1987 | Mullis |
| 4,786,600 A | 11/1988 | Kramer et al. |
| 4,800,159 A | 1/1989 | Mullis et al. |
| 4,868,105 A | 9/1989 | Urdea et al. |
| 5,124,246 A | 6/1992 | Urdea et al. |
| 5,130,238 A | 7/1992 | Malek et al. |
| 5,399,491 A | 3/1995 | Kacian et al. |
| 5,422,252 A | 6/1995 | Walker et al. |
| 5,437,990 A | 8/1995 | Burg et al. |
| 5,516,663 A | 5/1996 | Backman et al. |
| 5,532,129 A | 7/1996 | Heller |
| 5,547,861 A | 8/1996 | Nadeau et al. |
| 5,554,516 A | 9/1996 | Kacian et al. |
| 5,714,320 A | 2/1998 | Kool |
| 5,834,252 A | 11/1998 | Stemmer et al. |
| 6,022,686 A | 2/2000 | Garman et al. |
| 6,635,427 B2 | 10/2003 | Wittwer et al. |
| 8,198,026 B2 | 6/2012 | Chemeris et al. |
| 2002/0197611 A1 | 12/2002 | Chagovetz |
| 2006/0046265 A1 | 3/2006 | Becker et al. |
| 2007/0117125 A1 | 5/2007 | Chemeris et al. |
| 2010/0240103 A1 | 9/2010 | Mao et al. |
| 2012/0058481 A1 | 3/2012 | Ge et al. |
| 2012/0264643 A1 | 10/2012 | Chun et al. |
| 2013/0252238 A1 | 9/2013 | Robinson et al. |
| 2014/0213471 A1 | 7/2014 | Rajagopal et al. |

FOREIGN PATENT DOCUMENTS

| | | |
|---|---|---|
| CA | 2255531 A1 | 6/1999 |
| EP | 0320308 B1 | 11/1993 |
| WO | WO-8810315 A1 | 12/1988 |
| WO | WO-9309128 A1 | 5/1993 |
| WO | WO-03102239 A2 | 12/2003 |
| WO | WO-2006074222 A2 | 7/2006 |

(Continued)

OTHER PUBLICATIONS

Chehab, et al. Detection of specific DNA sequences by fluorescence amplification: a color complementation assay. Proc Natl Acad Sci USA. Dec. 1989;86(23):9178-82.

Chun, et al. Dual priming oligonucleotide system for the multiplex detection of respiratory viruses and SNP genotyping of CYP2C19 gene. Nucleic Acids Res. 2007;35(6):e40. Epub Feb. 7, 2007.

European search report and opinion dated Sep. 7, 2016 for EP Application No. 14743745.3.

(Continued)

*Primary Examiner* — Kenneth R Horlick
(74) *Attorney, Agent, or Firm* — Wilson Sonsini Goodrich & Rosati

(57) ABSTRACT

Methods of detecting at least one genetic variation in a polynucleotide analyte in a sample. A fluorophore is attached to a first primer, a quencher is attached to a second primer, the first primer and the second primer are specific for the polynucleotide analyte. A signal generated by the fluorophore and quencher is measured. PCR is performed with the first primer and the second primer using the polynucleotide analyte as a template, thereby amplifying the template. A signal generated by the fluorophore and quencher from the PCR amplification product is measured. Comparison is made of the signals; and a determination is made of the presence or absence of the at least one genetic variation based i) on the change in signal as determined; and ii) by comparing said change to the change in signal observed upon PCR amplification for a corresponding polynucleotide analyte lacking the at least one genetic variation.

23 Claims, 22 Drawing Sheets

Specification includes a Sequence Listing.

(56) References Cited

FOREIGN PATENT DOCUMENTS

| WO | WO-2007018734 A2 | 2/2007 |
| WO | WO-2007067151 A1 | 6/2007 |
| WO | WO-2006074222 A3 | 12/2007 |
| WO | WO-2008014485 A2 | 1/2008 |
| WO | WO-2008063194 A1 | 5/2008 |
| WO | WO-2009037438 A1 | 3/2009 |
| WO | WO-2012024642 A1 | 2/2012 |
| WO | WO-2014116884 A1 | 7/2014 |

OTHER PUBLICATIONS

Goodson, et al. LacI-DNA-IPTG loops: equilibria among conformations by single-molecule FRET. J Phys Chem B. Apr. 25, 2013;117(16):4713-22. doi: 10.1021/jp308930c. Epub Feb. 13, 2013.
Hennigan, et al. A FRET-based approach for studying conformational changes of a cytoskeleton-related tumor suppressor molecule. Methods Mol Biol. 2009;586:143-56. doi: 10.1007/978-1-60761-376-3_7.
Huang, et al. DNA-length-dependent fluorescence signaling on graphene oxide surface. Small. Apr. 10, 2012;8(7):977-83. doi: 10.1002/smll.201102156. Epub Feb. 10, 2012.
ICycler iQ™ Real-Time PCR Detection System Instruction manual. Bio-Rad. 2013.
International search report and written opinion dated May 13, 2014 for PCT Application No. PCT/US14-12836.
Jansen, et al. Development and evaluation of a four-tube real time multiplex PCR assay covering fourteen respiratory viruses, and comparison to its corresponding single target counterparts. J Clin Virol. Jul. 2001;51(3):179-85. doi: 10.1016/j.jcv.2011.04.010. Epub May 14, 2011.
Jaumot, et al. Resolution of a structural competition involving dimeric G-quadruplex and its C-rich complementary strand. Nucleic Acids Res. Jan. 5, 2006;34(1):206-16. Print 2006.
Lai, et al. PrimRglo: A multiplexable quantitative real-time polymerase chain reaction system for nucleic acid detection. Analytical Biochemistry.2012; 422:89-95.
Laurie, et al. Simultaneous digital quantification and fluorescence-based size characterization of massively parallel sequencing libraries. Biotechniques. Aug. 2013;55(2):61-7. doi: 10.2144/000114063.
Li, et al. Antiprimer quenching-based real-time PCR and its application to the analysis of clinical cancer samples. Clin Chem. Apr. 2006;52(4):624-33. Epub Feb. 9, 2006.
Merzouki, et al. Accurate and differential quantitation of HIV-1 tat, rev and nef mRNAs by competitive PCR. J Virol Methods. Dec. 1994;50(1-3):115-28. (abstract).
Perdok, et al. Protozoa Inhibitors to Reduce Methane Excretion From Dairy Cows. May 29, 2007. Available at: http://scholargoogle.co.th/scholar?g=PROTOZOA+INHIBITORS+TO+REDUCE+METHANE+EX CRETION+FROM+DAIRY+COWS&btnG=&hi=en&as_sdt=0%2C5. Accessed Apr. 10, 2014.
Real-time PCR handbook. Lifetime Technologies. 2012.
Vamosi, et al. Probing the conformation of DNA structures—4-way junctions and bulges—with fluorescence. Poster presented at the 11th International Biophysics Congress, Jul. 25-30, 1993, Budapest, Hungary.
Yeung, et al. Evaluation of dual-labeled fluorescent DNA probe purity versus performance in real-time PCR. Biotechniques. Feb. 2004;36(2):266-70, 272, 274-5.
Office action dated May 6, 2016 for U.S. Appl. No. 14/162,725.
Office action dated May 12, 2017 for U.S. Appl. No. 14/162,725.
Office action dated Nov. 7, 2016 for U.S. Appl. No. 14/162,725.

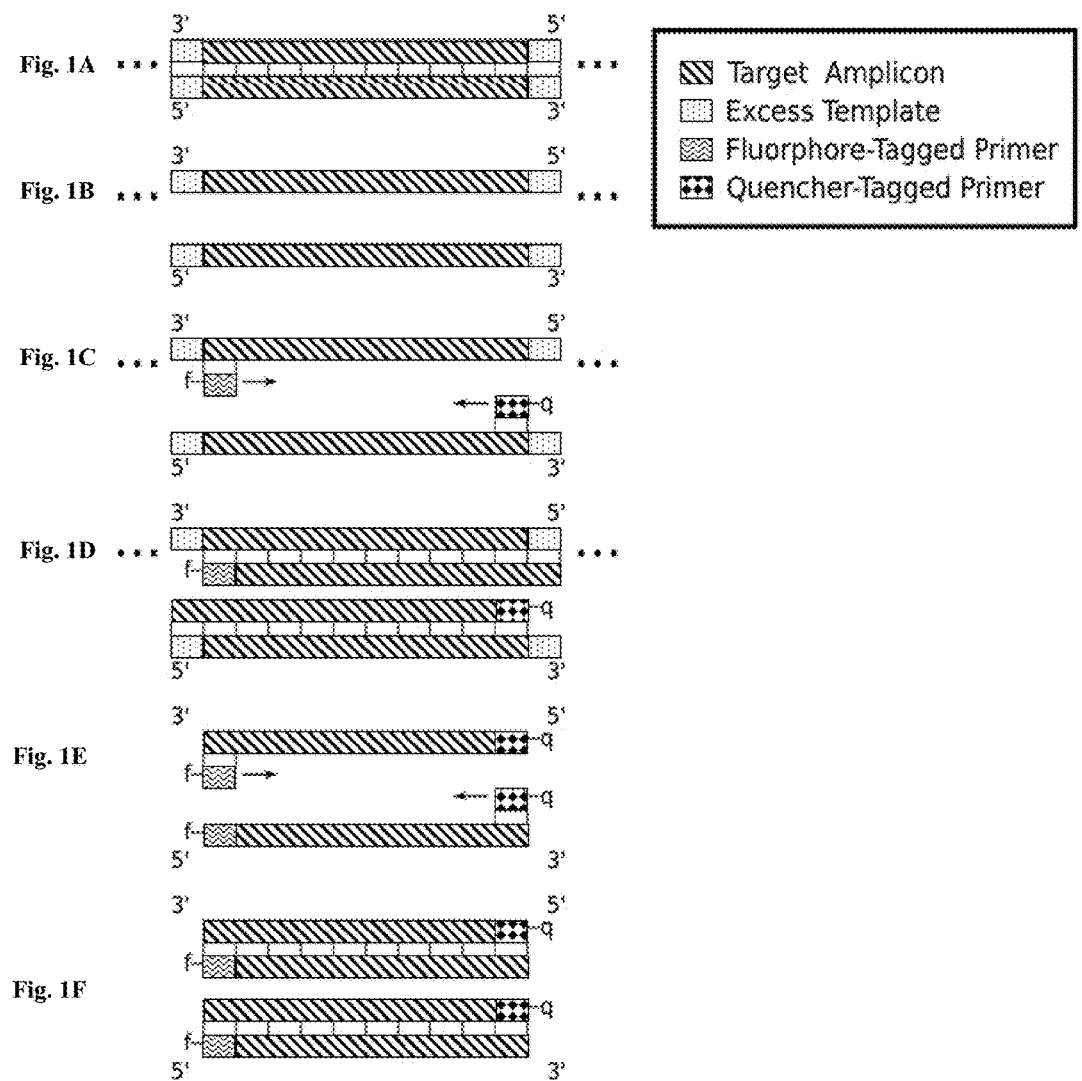

$$R_0^6 = \frac{9\,Q_0\,(\ln 10)\kappa^2 J}{128\,\pi^5 n^4 N_A}$$

$$E = \frac{1}{1 + (r/R_0)^6}$$

Fig. 9

| Target | Cy3 | Cy5 |
|---|---|---|
| HIV TPP 80mer | 1x [1um] | - |
| InfA 80mer | 2x [2um] | - |
| InfB 80mer | 4x [4um] | - |
| PIV-3 80mer | - | 1x [3um] |

Fig. 10A

5' ATGGGGGGGGGGGGGGGGATGGGGGGGGAAGGGGGGGATGGGGGGGGATGGGGATGGATG 3'
3' TACCCCCCCCCCCCCCCCTACCCCCCCCTTCCCCCCTACCCCCCCCCTACCCCTACCTAC 5'

Fig. 10B

FWD Primer /Quencher/5'ATGGGGGGGGGGGGGGGGAT3'
RWD Primer 3'CCCCCCCTACCCCTACCTAC5'/Fluorphore/

Fig. 10C

5' ATGGGGGGGGGGGGGGGGATGGGGGGGGAAGGGGGGGATGGGGGGGGATGGGGATGGATG 3'
                              Extension <-    3'CCCCCCCTACCCCTACCTAC5'/F/

3' TACCCCCCCCCCCCCCCCTACCCCCCCCTTCCCCCCTACCCCCCCCCTACCCCTACCTAC 5'
/Q/5'ATGGGGGGGGGGGGGGGGAT3'   -> Extension

Fig. 10D

/Q/5'ATGGGGGGGGGGGGGGGGATGGGGGGGGAAGGGGGGGATGGGGGGGGATGGGGATGGATG 3'
                              Extension <-    3'CCCCCCCTACCCCTACCTAC5'/F/

3' TACCCCCCCCCCCCCCCCTACCCCCCCCTTCCCCCCTACCCCCCCCCTACCCCTACCTAC 5'/F/
/Q/5'ATGGGGGGGGGGGGGGGGAT3'   -> Extension

Fig. 10E

/Q/5'ATGGGGGGGGGGGGGGGGATGGGGGGGGAAGGGGGGGATGGGGGGGGATGGGGATGGATG 3'
    3'TACCCCCCCCCCCCCCCCTACCCCCCCCTTCCCCCCTACCCCCCCCCTACCCCTACCTAC 5'/F/

/Q/5'ATGGGGGGGGGGGGGGGGATGGGGGGGGAAGGGGGGGATGGGGGGGGATGGGGATGGATG 3'
    3'TACCCCCCCCCCCCCCCCTACCCCCCCCTTCCCCCCTACCCCCCCCCTACCCCTACCTAC 5'/F/

Fig. 12

```
     5' ATGGGGGGGGGGGGGGGATGGGGGGGAAGGGGGGATGGGGGGGCATGGGGATGGATG 3' /Q2/
/Q1/ 3' TACCCCCCCCCCCCCCCCTACCCCCCCCTTCCCCCCTACCCCCCCCTACCCCTACCTAC 5'
         |                  |                              |
         f1                 f2                             f3
```

SEQUENCE LISTING

<160> NUMBER OF SEQ ID NOS: 52

<210> SEQ ID NO 1
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
ggaagctcta ttagatacag acacctgtca acataattgg                       40

<210> SEQ ID NO 2
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
ggaagctcta ttagatacag atgatacagt attagaagaa acacctgtca acataattgg    60

<210> SEQ ID NO 3
<211> LENGTH: 80
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
ggaagctcta ttagatacag atgatacagt attagaagaa atgagtttgc caggaagatg    60
acacctgtca acataattgg                                              80

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ggaagctcta ttagatacag                                              20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 5
ccaattatgt tgacaggtgt                                              20

<210> SEQ ID NO 6
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gtagggatag acccttttcaa actgcttcaa aacagccaag tatacagcct aatcagaccg    60
aatgagaatc cagcacacaa gagtc                                        85

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gtagggatag acccttttcaa actg                                        24

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gactcttgtg tgctggattc tc                                           22

<210> SEQ ID NO 9
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
agccaagtat acagcctaat cagaccga                                     28

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gtagggatag acccttttcaa actg                                        24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence: Synthetic
```

```
                            primer

<400> SEQUENCE: 11
gactcttgtg tgctggattc tc                                          22

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gtagggagag acccttcaa actg                                         24

<210> SEQ ID NO 13
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
gtgcttccca taagcattta cgccaaaata cctcaactag ggttcaacgt tgaagagtac  60
tctatggttg ggtatgaagc c                                           81

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgcttccca taagcattta cg                                          22

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggcttcatac ccaaccatag ag                                          22

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
cctcaactag ggttcaacgt tgaagagt                                    28

<210> SEQ ID NO 17
<211> LENGTH: 22
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 17
gtgcttccca taagcattta cg                                              22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggcttcatac ccaaccatag ag                                              22

<210> SEQ ID NO 19
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
gttggaaact acacacatct cctctatgta caaccaacac aaaggaagga tccaacatct     60
gcttaacaag aaccgacaga ggatg                                           85

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gttggaaact acacacatct cctc                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
catcctctgt cggttcttgt taag                                            24

<210> SEQ ID NO 22
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
ccaacacaaa ggaaggatcc aacatctg                                        28

<210> SEQ ID NO 23
<211> LENGTH: 24
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 23
gttggaaact acacacatct cctc                                              24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
catcctctgt cggttcttgt taag                                              24

<210> SEQ ID NO 25
<211> LENGTH: 81
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 25
cctcacctca agtcagaaca taactgagga gttttaccaa tcgacatgta gtgcagttag       60
cagaggttac ttgagtgctt t                                                 81

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
cctcacctca agtcagaaca taac                                              24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
aaagcactca gtaacctct gc                                                 22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 28
accaatcgac atgtagtgca gt                                                22

<210> SEQ ID NO 29
<211> LENGTH: 24
<212> TYPE: DNA
```

<213> ORGANISM: Artificial Sequence
<220> FEATURE:
<223> OTHER INFORMATION: Description of Artificial Sequence: Synthetic
      primer

<400> SEQUENCE: 29
cctcacctca agtcagaaca taac                                         24

<210> SEQ ID NO 30
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
aaagcactca agtaacctct gc                                           22

<210> SEQ ID NO 31
<211> LENGTH: 85
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
acaatggaca aggtgtgaag agccccgtgt gctcgctttg agtcctccgg cccctgaatg    60
tggctaacct taaccctgca gctag                                        85

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
acaatggaca aggtgtgaag ag                                           22

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
ctagctgcag ggttaaggtt ag                                           22

<210> SEQ ID NO 34
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 34
tgtgctcgct ttgagtcctc cg                                           22

<210> SEQ ID NO 35
<211> LENGTH: 22

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
acaatggaca aggtgtgaag ag                                               22

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ctagctgcag ggttaaggtt ag                                               22

<210> SEQ ID NO 37
<211> LENGTH: 88
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gagagcattg agaacagtca ggccttggtg gatcaatcaa acagaatcct aagcagtgca      60
gagaaaggaa acactggctt catcattg                                         88

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gagagcattg agaacagtca gg                                               22

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caatgatgaa gccagtgttt cc                                               22

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
acagaatcct aagcagtgca gaga                                             24

<210> SEQ ID NO 41
```

```
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
gagagcattg agaacagtca gg                                             22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
caatgatgaa gccagtgttt cc                                             22

<210> SEQ ID NO 43
<211> LENGTH: 86
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
tcgagagtga acccagtcat aacttactca acagcaaccg aaagagtaaa cgagctggcc    60
atccgaaaca gaacactctc agctgg                                         86

<210> SEQ ID NO 44
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
tcgagagtga acccagtcat aa                                             22

<210> SEQ ID NO 45
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
ccagctgaga gtgttctgtt tc                                             22

<210> SEQ ID NO 46
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ccgaaagagt aaacgagctg gcca                                           24
```

```
<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 47
ccgaaagagt aaacgagctg gcca                                          24

<210> SEQ ID NO 48
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
ccgaaagagt aaacgagctg gcca                                          24

<210> SEQ ID NO 49
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 49
ccgaaagagt aaacgagctg gcca                                          24

<210> SEQ ID NO 50
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atgggggggg ggggggggat gggggggaa gggggggatgg gggggatgg ggatggatg     59

<210> SEQ ID NO 51
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atgggggggg ggggggggat                                               20

<210> SEQ ID NO 52
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
catccatccc catccccccc                                               20
```

US 10,081,844 B2

CHROMOPHORE-BASED PCR METHODS FOR DETECTING AND CHARACTERIZING NUCLEIC ACIDS IN SAMPLES

CROSS-REFERENCE

This application is a continuation application of U.S. patent application Ser. No. 14/162,725 filed on Jan. 23, 2014, now abandoned, which claims the benefit of U.S. provisional application 61/756,343, filed Jan. 24, 2013, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Oct. 6, 2017, is named 38075-719_301_SL.txt and is 12,793 bytes in size.

BACKGROUND OF THE INVENTION

Nucleic acid analyte identification is a critical procedure in a variety of biomedical applications, such as in research and clinical diagnostic environments. Identification of an analyte is primarily done by sequencing or by amplification-based detection. For example, in the latter scheme, the polymerase chain reaction is often used to increase the quantity of the nucleic acid analyte present. Then, the nucleic acid analytes are discriminated using one of several additional techniques including fluorescence intensity measurement (e.g., fluorescent probes or intercalating dyes), length discrimination (e.g., using gel electrophoresis or melt curve analysis), or chromatography (e.g., haptin-based nucleic acid capture). Thus, current amplification-based detection technology indirectly detects analytes and requires a secondary technique (such as gel electrophoresis or mass spectroscopy) for analyte detection. Amplification or polymerization-based techniques that directly detect analytes would improve efficiency, time and cost.

SUMMARY OF THE INVENTION

Disclosed herein are methods, compositions, and kits for detecting analytes, particularly polynucleotides and/or polypeptides. The methods generally involve using oligonucleotides (e.g., primers, probes) attached to chromophores (e.g., fluorophores, quenchers, etc.) in amplification or polymerization reactions in order to detect a polynucleotide analyte. In some embodiments, provided herein are methods of detecting at least one polynucleotide analyte in a sample, comprising: (a) combining the sample with a first primer and a first oligonucleotide, wherein a first chromophore is attached to the first primer, a second chromophore is attached to the first oligonucleotide, the first primer and the first oligonucleotide are specific for a first polynucleotide analyte and the first chromophore is different from the second chromophore; (b) measuring a first signal generated by the first and second chromophores; (c) performing at least one polymerization reaction with the first primer using the first polynucleotide analyte as a template; and (d) measuring a second signal generated by the first and second chromophores; wherein the first and second signals are used to detect the first polynucleotide analyte.

In some cases, the first oligonucleotide is a second primer. In some cases, the first chromophore is attached to the 5' end of the first primer. In some cases, the first chromophore is an inorganic or organic dye, a fluorophore or a quencher. In some cases, the first chromophore is a fluorophore. In some cases, the fluorophore is 6-FAM (Fluorescein), 6-FAM (NHS Ester), Fluorescein dT, HEX, JOE (NETS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705. In some cases, the second chromophore is attached to the 5' end of the second primer. In some cases, the second chromophore is an inorganic or organic dye, a fluorophore or a quencher. In some cases, the second chromophore is a quencher. In some cases, the quencher is Iowa Black FG, Iowa Black RG, BHQ1, BHQ2 or BHQ3. In some cases, the first chromophore is a fluorophore and the second chromophore is a quencher.

In some cases, the methods described herein further comprising comparing the first and second signals, wherein a change in the first and second signals indicates the presence of the first polynucleotide analyte. In some cases, the change in the first and second signals is a decrease in fluorescent intensity. In some cases, the change is an increase in intensity. In some cases, the decrease in fluorescent intensity is at least about a 30% decrease in signal (or at least about 10%, 20%, 30%, 35%, 40%, 45%, 50%, 55%, 60%, or 75%). In some cases, the second signal is measured after a second polymerization reaction. In some cases, the polymerization reaction is a polymerase chain reaction process or an isothermal process. In some cases, the polymerase chain reaction process is an end-point polymerase chain reaction process, a real-time polymerase chain reaction process, a digital polymerase chain reaction process, a droplet digital polymerase chain reaction process, or a quantitative polymerase chain reaction process. In some cases, the first primer is a forward primer and the second primer is a reverse primer. In some cases, the first primer is a reverse primer and the second primer is a forward primer. In some cases, the first and second chromophores interact through an electron-transfer process. In some cases, the first polynucleotide analyte is from about 10 to about 500 nucleotides in length. In some cases, the concentration of the first polynucleotide analyte is from about 10 µM to about 10 aM. In some cases, the first polynucleotide analyte is a DNA polynucleotide analyte. In some cases, the first polynucleotide analyte is an RNA polynucleotide analyte.

In some cases, the first polynucleotide analyte comprises a genetic variation. In some cases, the genetic variation comprises a substitution, an addition, a deletion or a translocation. In some cases, the genetic variation comprises a single-nucleotide polymorphism (SNP). In some cases, the at least one polynucleotide analyte is from a source selected from a human, a non-human mammal, a plant, a bacteria, a fungus, an archaea, a parasite, or a virus. In some cases, the virus is a human immunodeficiency virus, an influenza type A virus, an influenza type B virus, a respiratory syncytial virus type A (RsvA), a respiratory syncytial virus type B virus (RsvB), a human rhinovirus (Hrv), a human metapneumovirus (Hmpv) or a human parainfluenza virus type 3 (PIV-3). In some cases, the sample is a forensic sample, a clinical sample, a food sample, an environmental sample, a pharmaceutical sample, or a sample from a consumer product. In some cases, the methods disclosed herein further comprising detecting at least one additional polynucleotide analyte within the sample with an additional fluorophore attached to a primer, wherein the first chromophore is a fluorophore with the same color as the additional fluorophore. In some cases, the first primer is not attached to two or more chromophores. In some cases, the first oligonucleotide is not attached to two or more chromophores. In some cases, step b) of the method further comprises measuring the first signal at a first denaturing step and a third signal at a first annealing step; step d) further comprises measuring the second signal at a second denaturing step and a fourth signal at a second annealing step; and the method further comprises comparing the first signal with the second signal to obtain a first ratio and comparing the third signal with the fourth signal to obtain a second ratio; wherein when the first ratio is about 1 and the second ratio is greater than or less than 1 indicate the presence of the first polynucleotide analyte.

In some cases, step a) of the method described herein further comprises combining the sample with a third primer and a second oligonucleotide, wherein a third chromophore is attached to the third primer and a fourth chromophore is attached to the second oligonucleotide, and the third primer and the second oligonucleotide are specific for a second polynucleotide analyte; step b) further comprises measuring a fifth signal generated by the third and fourth chromophores; step d) further comprises measuring a sixth signal generated by the third and fourth chromophores; wherein the fifth and sixth signals are used to detect the second polynucleotide analyte. In some cases, the methods disclosed herein further comprising comparing the fifth and sixth signals, wherein a change in the fifth and sixth signals indicates the presence of the second polynucleotide analyte. In some cases, the second oligonucleotide is a fourth primer.

Also disclosed herein are methods of detecting at least one genetic variation in an analyte comprising: (a) combining a first analyte with a first primer and a second primer, wherein a first chromophore is attached to the first primer, a second chromophore is attached to the second primer, at least one of the first and the second primers are specific for a first genetic variation in the first analyte and the first chromophore is different from the second chromophore; (b) measuring a first signal generated by the first and second chromophores; (c) performing at least one polymerization reaction with the first primer and the second primer using the first analyte as a template; and (d) measuring a second signal generated by the first and second chromophores; wherein the first and second signals are used to detect the first genetic variation in the first analyte. In some cases, the methods described herein further comprise comparing the first and second signals, wherein a change in the first and second signals indicates the presence of the genetic variation in the first analyte.

In some cases, the analyte is a polynucleotide analyte. In some cases, the genetic variation comprises a substitution, an addition, a deletion or a translocation. In some cases, the genetic variation comprises a single-nucleotide polymorphism (SNP). In some cases, the first primer comprises a sequence encoding the SNP or the first primer binds to a region of the analyte encoding the SNP. In some cases, the second primer comprises a sequence not encoding the SNP or the second primer comprises a sequence complementary to a region of the analyte not encoding the SNP. In some cases, the first primer encodes a region of the analyte less than 500 base pairs apart from a region of the analyte encoded by the second primer. In some cases, the change in signal is distinct for at least two of the mismatched base pairs selected from the group consisting of UU, UT, UG, UC, UA, AA, TT, GG, CC, AG, AC, TG and TC. In some cases, the change in signal from a mismatched base pair is distinct from a change in signal from a complementary base pair.

In some cases, step a) of the methods described herein further comprises combining the first analyte with a third primer and a fourth primer, wherein a third chromophore is attached to the third primer, a fourth chromophore is attached to the fourth primer, the third and the fourth primers are specific for a second genetic variation in the first analyte and the third chromophore is different from the fourth chromophore; step b) further comprises measuring a third signal; step d) further comprises measuring a fourth signal; and the method further comprises comparing the third and fourth signals; wherein a change in the third and fourth signals indicates the presence of the second single genetic variation in the first analyte. In some cases, step a) of the method further comprises combining a second analyte with a third primer and a fourth primer, wherein a third chromophore is attached to the third primer, a fourth chromophore is attached to the fourth primer comprises, the third and the fourth primers are specific for a second genetic variation in the second analyte and the third chromophore is different from the fourth chromophore; step b) further comprises measuring a third signal; step d) further comprises measuring a fourth signal; and the method further comprises comparing the third and fourth signals; wherein a change in the third and fourth signals indicates the presence of the second single genetic variation in the second analyte. In some cases, step a) further comprises combining a second analyte with a third primer and a fourth primer, wherein the first chromophore is attached to the third primer, the second chromophore is attached to the fourth primer, and the third and the fourth primers are specific for a second genetic variation in the second analyte. In some cases, the polymerization reaction is a PCR process or an isothermal reaction. In some cases, the PCR process is an end-point PCR process, a digital PCR process, a real-time PCR process, a droplet digital PCR process, or a quantitative PCR process. In some cases, the polymerization reaction is a quantitative PCR process. In some cases, the detecting comprises a quantitative PCR method. In some cases, the detecting comprises a quantitative PCR method and a second method. In some cases, the second method is a digital PCR process. In some cases, at least one SNP is detected in a gene. In some cases, at least one SNP is associated with a disease. In some cases, the disease is a genetic disorder, an autoimmune disease, a neurological disease, a cardiovascular disease, or a cancer.

Also disclosed herein are methods of detecting a plurality of analytes, comprising: a) combining the plurality of analytes with a plurality of primer pairs, wherein each primer pair is specific to a single analyte and each primer of the primer pair is attached to at least one chromophore; b) measuring a first set of signals generated by the chromophores; c) performing at least one polymerization reaction with the plurality of primer pairs using the plurality of analytes as templates; and d) measuring a second set of signals generated by the chromophores; wherein the first and second set of signals are used to detect each analyte of the plurality of analytes. In some cases, the method described herein further comprises: e) repeating step c and d at least once; and f) generating a set of signature profiles; wherein the presence of each analyte of the plurality of analytes is detected by comparing the set of signature profiles to a control set of signature profiles.

In some cases, the signature profile is an end-point signature profile or a signature curve. In some cases, the plurality of analytes has different lengths. In some cases, each of the plurality of primer pairs comprises a forward primer and a reverse primer. In some cases, one, two or more chromophores are attached to the forward primer. In some cases, one chromophore is attached to the 5' end of the forward primer. In some cases, at least one chromophore is attached to the reverse primer. In some cases, one chromophore is attached to the 5' end of the reverse primer. In some cases, the chromophore is an inorganic or organic dye, a fluorophore or a quencher. In some cases, the chromophore is a fluorophore. In some cases, the chromophore is a quencher.

Also disclosed herein are methods of generating a signature curve profile for a polynucleotide analyte, comprising: (a) contacting the polynucleotide analyte with a first primer and a second primer, wherein a first chromophore is attached to the first primer and a second chromophore is attached to the second primer, the first primer and the second primer are specific for the polynucleotide analyte and the first chromophore is different from the second chromophore; (b) measuring a first signal at a first temperature; (c) performing at least one polymerization reaction with the first primer and the second primer using the polynucleotide analyte as a template; (d) measuring a second signal at the first temperature; and (e) repeating step c and d at least once; wherein the signals create the signature curve profile of the polynucleotide analyte. In some cases, the method disclosed herein further comprises: f) changing the temperature; g) measuring a third signal at a second temperature; and h) repeating steps f and g at least once; wherein the signals create the signature curve profile of the polynucleotide analyte.

In some cases, the signature curve is a length curve, a morphology curve, a melt curve, or a SNP curve. In some cases, the polymerization reaction is a polymerase chain reaction process. In some cases, the polymerase chain reaction process is an end-point polymerase chain reaction process, a real-time polymerase chain reaction process, a digital polymerase chain reaction process or a quantitative polymerase chain reaction process. In some cases, the first chromophore is an inorganic or organic dye, a fluorophore or a quencher. In some cases, the first chromophore is a fluorophore. In some cases, the fluorophore is 6-FAM (Fluorescein), 6-FAM (NHS Ester), Fluorescein dT, HEX, JOE (NHS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705. In some cases, the second chromophore is an inorganic or organic dye, a fluorophore or a quencher. In some cases, the second chromophore is a quencher. In some cases, the quencher is Iowa Black FG, Iowa Black RG, BHQ1, BHQ2 or BHQ3. In some cases, the polynucleotide analyte is a DNA polynucleotide analyte. In some cases, the polynucleotide analyte is an RNA polynucleotide analyte. In some cases, the polynucleotide analyte is from a source selected from the group consisting of a human, a non-human mammal, a plant, a bacteria, an archaea, a fungus, a parasite, and a virus. In some cases, the virus is a human immunodeficiency virus, an influenza type A virus, an influenza type B virus, a respiratory syncytial virus type A (RsvA), a respiratory syncytial virus type B virus (RsvB), a human rhinovirus (Hrv), a human metapneumovirus (Hmpv) or a human parainfluenza virus type 3 (PIV-3).

Also disclosed herein is a method of monitoring an amplification reaction comprising: (a) contacting a first polynucleotide analyte with: i) a first primer and a second primer, wherein the first primer and the second primer are specific for the first polynucleotide analyte; and ii) at least two chromophores capable of specific incorporation into a product amplified from the first polynucleotide analyte; (b) subjecting the combination in step (a) to a temperature capable of denaturing double-stranded DNA; (c) measuring a first signal in step (b) generated by the at least two chromophores; (d) subjecting the combination in step b) to a temperature capable of annealing polynucleotides; (e) measuring a second signal in step (d) generated by the at least two chromophores; and (f) repeating steps b)-e) to obtain a third signal and a fourth signal; and (g) comparing the first and the third signals to obtain a first ratio and the second and the fourth signals to obtain a second ratio; wherein an amplification reaction occurs when the first ratio is about 1 and the second ratio is greater than or less than 1. In some cases, at least one chromophore is attached to the first primer, for example exactly one chromophore may be attached to the first primer. In some cases, one chromophore (or exactly one chromophore) is attached to the 5' end of the first primer. In some cases, one, two or more chromophores are attached to the second primer. In some cases, one chromophore is attached to the 5' end of the second primer. In some cases, the chromophore is an inorganic or organic dye, a fluorophore or a quencher.

Also disclosed herein are methods of detecting a morphology of an analyte, comprising: (a) providing a sample comprising the analyte, wherein a first chromophore, a second chromophore and a third chromophore are attached to the analyte, wherein the first, second and third chromophores are different; (b) measuring a signal from the first chromophore, second chromophore and the third chromophore at a first and second temperature, wherein the first and second temperatures are different; and (c) using the measured signals to detect the morphology of the analyte. In some cases, the analyte is a protein, a polypeptide, a lipid or a polynucleotide. In some cases, the analyte is a polynucleotide. In some cases, the polynucleotide is a DNA polynucleotide. In some cases, the polynucleotide is an RNA polynucleotide. In some cases, the first chromophore is an inorganic or organic dye, a fluorophore or a quencher. In some cases, the first chromophore is a first fluorophore. In some cases, the first fluorophore is 6-FAM (Fluorescein), 6-FAM (NHS Ester), Fluorescein dT, HEX, JOE (NHS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705. In some cases, the second chromophore is an inorganic or organic dye, a fluorophore or a quencher. In some cases, the second chromophore is a second fluorophore. In some cases, the second fluorophore is 6-FAM (Fluorescein), 6-FAM (NHS Ester), Fluorescein dT, HEX, JOE (NHS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705. In some cases, the third chromophore is an inorganic or organic dye, a fluorophore or a quencher. In some cases, the third chromophore is a quencher. In some cases, the quencher is Iowa Black FG, Iowa Black RG, BHQ1, BHQ2 or BHQ3. In some cases, the analyte comprises more than one fluorophore. In some cases, the analyte comprises more than one quencher. In some cases, the polynucleotide comprises a quencher at its 3' end.

Also disclosed herein are methods of detecting a polynucleotide analyte comprising: (a) combining the polynucleotide analyte with at least two chromophores, wherein the at least two chromophores are each attached to a separate polynucleotide that is complementary to a region within the polynucleotide analyte; (b) performing at least one polymerization reaction to incorporate the at least two chromophores into products of the polymerization reaction; and (c) detecting a fluorescent intensity from the at least two chromophores at a first timepoint and a second timepoint, wherein the second timepoint is later than the first timepoint and wherein a change (particularly a decrease) in fluorescent intensity at the second timepoint relative to the first timepoint is indicative of the presence of the polynucleotide analyte. In some cases, the polymerization reaction is a polymerase chain reaction. In some cases, the first timepoint is after step a) and the second timepoint is after step b). In some cases, the products of the at least one polymerization reaction each comprise a first polynucleotide strand and a second polynucleotide strand, wherein the first polynucleotide strand and the second polynucleotide strand are complementary. In some cases, the at least two chromophores are different. In some cases, the at least two chromophores comprise a fluorophore. In some cases, the at least two chromophores comprise a fluorophore and a quencher. In some cases, the fluorophore is incorporated into the first polynucleotide strand and the quencher is incorporated into the second polynucleotide strand. In some cases, the fluorophore is incorporated at the 5' end of first polynucleotide strand and the quencher is incorporated at the 5' end of the second polynucleotide strand.

Also disclosed herein are compositions and kits, particularly for detecting polynucleotide or polypeptide analytes. In some cases, the kits comprise oligonucleotides (e.g., primers, probes, etc.) attached to a chromophore (e.g., fluorophore, quencher). In some cases, the kit comprises: (a) a first primer or probe attached to a fluorophore; and (b) a second primer or probe attached to a quencher. In some cases, the kit comprises: (a) a first primer or probe attached to exactly one first chromophore, wherein the first chromophore is a fluorophore; and (b) a second primer or probe attached to exactly one second chromophore, wherein the first chromophore is different from the second chromophore. In some cases, the second chromophore is a quencher. In some cases, the second chromophore is a fluorophore. In some cases, the first primer or probe is a primer. In some cases, the second primer or probe is a primer. In some cases, the first primer or probe comprises an oligonucleotide sequence that is complementary to the sequence of a target analyte. In some cases, the second primer or probe comprises an oligonucleotide sequence complementary to the sequence of a target analyte. In some cases, the fluorophore is 6-FAM (Fluorescein), 6-FAM (NHS Ester), Fluorescein dT, HEX, JOE (NHS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705. In some cases, the quencher is Iowa Black FG, Iowa Black RG, BHQ1, BHQ2 or BHQ3. In some cases, the kit comprises at least three primers, wherein each primer is attached to a different chromophore.

In some cases, the kit comprises: (a) a first primer or probe attached to a first chromophore, wherein the first chromophore is a fluorophore; and (b) a second primer or probe attached to a second chromophore, wherein the first chromophore is different from the second chromophore. In some cases, the kit comprises: (a) a first primer or probe attached to exactly one first chromophore; and (b) a second primer or probe attached to exactly one second chromophore, wherein the first chromophore is different from the second chromophore. In some cases, the kit comprises: (a) a first primer or probe attached to exactly one first chromophore, wherein the first chromophore is a fluorophore; and (b) a second primer or probe attached to exactly one second chromophore, wherein the first chromophore is different from the second chromophore. In some cases, the second chromophore is a quencher. In some cases, the second chromophore is a fluorophore. In some cases, the first primer or probe is a primer. In some cases, the second primer or probe is a primer. In some cases, the first primer or probe comprises an oligonucleotide sequence that is complementary to the sequence of a target analyte. In some cases, the second primer or probe comprises an oligonucleotide sequence complementary to the sequence of a target analyte. In some cases, the fluorophore is 6-FAM (Fluorescein), 6-FAM (NHS Ester), Fluorescein dT, HEX, JOE (NHS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705. In some cases, the quencher is Iowa Black FG, Iowa Black RG, BHQ1, BHQ2 or BHQ3. In some cases, the kit comprises at least three primers, wherein each primer is attached to a different chromophore.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

Various aspects of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1 exemplifies a mechanism for detection of a nucleic acid analyte using chromophore-attached primers (a fluorophore-attached forward (FWD) primer and a quencher-attached reverse (or rewind (RWD)) primer) during a polymerase chain reaction (PCR). FIGS. 1A-1B illustrate the denaturation of a double-stranded polynucleotide analyte. FIGS. 1C-1D illustrate the annealing of the chromophore-attached primers to opposite strands of the analyte and for a polymerase to extend the primers during a PCR reaction. FIGS. 1E-1F illustrate the formation of a double-stranded PCR product containing both chromophores (fluorophore and a quencher) which leads to the generation of a signal (e.g., quenching of fluorescence).

FIG. 2A illustrates an energy transfer formula. FIG. 2B illustrates a Jablonski diagram showing Förster resonance energy transfer with typical timescales indicated.

FIG. 5A illustrates the qPCR detection of 80 bp HIV TPP analytes at 10 nM concentration. FIG. 5B illustrates the qPCR detection of 80 bp HIV TPP analytes at 1 nM concentration. FIG. 5C illustrates the qPCR detection of 80 bp HIV TPP analytes at 100 pM concentration. FIG. 5D illustrates the qPCR detection of 80 bp HIV TPP analytes at 10 pM concentration. All successful detection curves exhibit the inverse-sigmoidal characteristic.

FIG. 6A illustrates the qPCR detection of 80 bp HIV TPP analytes at 1 pM concentration. FIG. 6B illustrates the qPCR detection of 80 bp HIV TPP analytes at 100 fM concentration. FIG. 6C illustrates the qPCR detection of 80 bp HIV TPP analytes at 10 fM concentration. FIG. 6D illustrates the qPCR detection of 80 bp HIV TPP analytes at 1 fM concentration.

FIG. 7A illustrates the extent of quenching using a 40 mer analyte. FIG. 7B illustrates the extent of quenching using a 60 mer analyte. FIG. 7C illustrates the extent of quenching using a 80 mer analyte.

FIG. 9 exemplifies the binary coding of analytes. Analytes in a 3-plex CY3 assay were coded using binary spaced primer concentrations. A TaqMan positive control sequence was amplified in each reaction to confirm that the PCR performed successfully.

FIG. 10A-FIG. 10E exemplify an amplification or polymerization reaction using a polymerase chain reaction (PCR) to detect an analyte. FIG. 10A illustrates the sequence of the analyte (Analyte 01) to be detected (SEQ ID NO: 50). FIG. 10B illustrates a forward (FWD) and a reverse (RWD) primer pair specific for Analyte 01 (SEQ ID NOs: 51-52, respectively, in order of appearance). FIG. 10C illustrates the annealing step during the first cycle of the PCR reaction (SEQ ID NOs: 50, 52 and 51, respectively, in order of appearance). FIG. 10D illustrates the annealing step during the second cycle of the PCR reaction (SEQ ID NOs: 50, 52 and 51, respectively, in order of appearance). FIG. 10E illustrates the extended PCR products after the second extension cycle (SEQ ID NO: 50).

FIG. 12 exemplifies the incorporation of multiple chromophores into an analyte in order to determine its morphology (SEQ ID NO: 50).

FIG. 13A illustrates the morphology of the oligonucleotide at a first temperature ($T_1$). Three fluorophores ($F_1$, $F_2$ and $F_3$) are attached to the oligonucleotide and one quencher ($Q_1$) is attached at the 3' end of the oligonucleotide. FIG. 13B illustrates the fluorescence signature profile of the oligonucleotide at $T_1$. At $T_1$, Q1 is closest to $F_3$, and a quenching effect is observed (FIG. 13B). FIG. 13C illustrates the morphology of the oligonucleotide at a second temperature ($T_2$). FIG. 13D illustrates the fluorescence signature profile of the oligonucleotide at $T_2$. At $T_2$, the oligonucleotide is fully denatured and $Q_1$ is further away from $F_3$. As a result, the fluorescence signal of $F_3$ increased (FIG. 13D).

DETAILED DESCRIPTION OF THE INVENTION

Figures 2A, 2B:
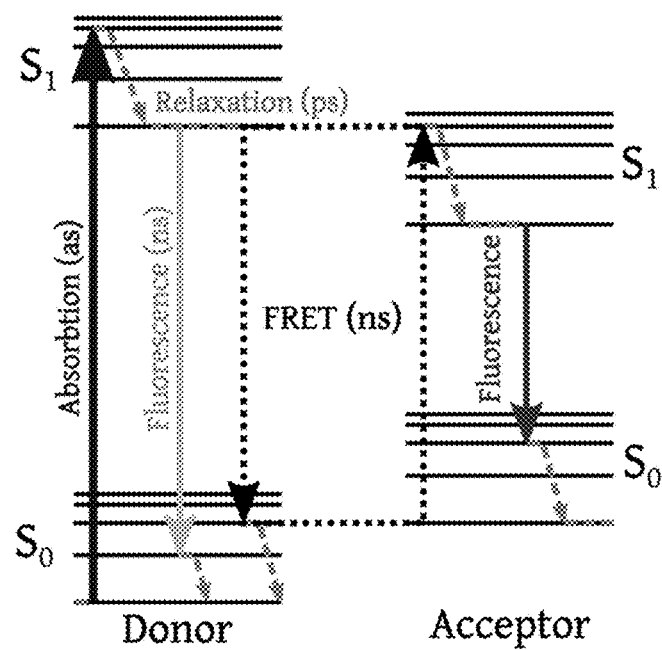
FIG. 2A-FIG. 2B exemplify an electron transfer state.

Provided herein are methods, systems, compositions, and kits for the detection of one or more analytes using chromophore-attached oligonucleotides (e.g., primers and/or probes) specific for an analyte. For example, the incorporation of chromophores into an amplification or polymerization product (e.g., through the use of forward and reverse primers that are attached to different chromophores as illustrated, e.g., in FIG. 1) provides a number of advantages.

For example, methods described herein can provide for the direct detection of one or more analytes in a single reaction (such as an amplification reaction (such as a PCR reaction or PCR reaction process) or a polymerization reaction). In addition, the direct incorporation of chromophores into the amplification or polymerization product (e.g., the analyte) allows for more accurate quantification of the analyte and for the real-time monitoring of the progression of an amplification or polymerization reaction. For example, once the analyte has been amplified to incorporate two different chromophores, upon excitation of one chromophore, an electron may travel through the pi-bond network of a DNA backbone to interact with a second chromophore, thereby generating a detectable signal or change in signal.

Methods described herein are particularly suitable for detecting genetic variations, such as single nucleotide polymorphisms (SNPs) or other qualitative information of an analyte. In some cases, a single base-pair mismatch between a chromophore-attached primer and the analyte can be detected upon amplification or polymerization of the analyte (or polymerization or extension of the primer). For example, a change in signal may occur if there is a disruption in a contiguous double-stranded DNA sequence upon amplification or polymerization of the analyte (or polymerization or extension of the primer (e.g., the primer specific for the SNP)) when a SNP is present. A single base pair misalignment (e.g. internal misalignment (such as a SNP) or terminal overhangs) can result in significant decrease in signal compared to the signal generated upon amplification or polymerization of the analyte (or polymerization or extension of the primer) without a base pair misalignment due to a disruption in electron transport between chromophores incorporated into an analyte containing a base pair misalignment.

Additionally described herein are methods to normalize signals during an amplification or polymerization reaction, such as a PCR reaction (or PCR reaction process). In some cases, the methods described herein can provide for a cycle-by-cycle normalization of a PCR reaction or process (e.g. chopper stabilization where individual cycles are reset to a reference value). For example, in some cases, when a signal measured during the denaturing step of a cycle is within a reference signal range, the denaturation signal can be used to normalize the signal measured during the annealing step of the same cycle. Thereby, the cycle-by-cycle normalization can provide a means to determine the reliability of the PCR reaction and can be used with the detection methods described herein to provide particularly accurate detection and measurements of analytes.

Also described herein are methods which allow detection of analytes present in low concentrations. In some cases, the sensitivity of the methods described herein can detect analytes at concentrations of about 10 uM to about 1 aM. In some cases, the methods provided herein can be combined with a digital amplification or polymerization process (e.g. droplet digital PCR), to further enhance the detection. In some cases, the methods provided herein can be used to detect analytes that are present at a trace concentration in a sample (e.g. a rare SNP).

Further described herein are methods to detect of multiple analytes in a single reaction or experiment, without the need to resort to additional experiments or materials (e.g. reagents). Thereby, the disclosed methods can reduce or eliminate the associated cost of additional reagents or materials and increase time and efficiency.

I. Certain Terminology

It is to be understood that the foregoing general description and the following detailed description are exemplary and explanatory only and are not restrictive of any subject matter claimed. In this application, the use of the singular includes the plural unless specifically stated otherwise. It must be noted that, as used in the specification and the appended claims, the singular forms "a," "an" and "the" include plural referents unless the context clearly dictates otherwise. In this application, the use of "or" means "and/or" unless stated otherwise. Furthermore, use of the term "including" as well as other forms, such as "include," "includes," and "included," is not limiting.

The term "about," as used herein, generally refers to a range that is 15% greater than or less than a stated numerical value within the context of the particular usage. For example, "about 10" would include a range from 8.5 to 11.5.

The term "primer," as used herein, generally refers to a short linear oligonucleotide that hybridizes to a target nucleic acid sequence (e.g., a DNA template to be amplified) to prime a nucleic acid synthesis reaction. The primer may be an RNA oligonucleotide, a DNA oligonucleotide, or a chimeric sequence. The primer may contain natural, synthetic, or nucleotide analogues (e.g., those that increase $T_m$). Both the upper and lower limits of the length of the primer are empirically determined. The lower limit on primer length is the minimum length that is required to form a stable duplex upon hybridization with the target nucleic acid under nucleic acid amplification or polymerization reaction conditions. Very short primers (usually less than 3 nucleotides long) do not form thermodynamically stable duplexes with target nucleic acid under such hybridization conditions. The upper limit is often determined by the possibility of having a duplex formation in a region other than the pre-determined nucleic acid sequence in the target nucleic acid. Generally, suitable primer lengths are in the range of about 3 nucleotides long to about 40 nucleotides long. The "primers" used in the methods of amplification or polymerization of a target nucleic acid described herein will be of a length appropriate for a particular set of experimental conditions. The determination of primer length is well within the routine capabilities of those of skilled in the art.

The terms "polynucleotide," "oligonucleotide," or "nucleic acid," as used herein, are used herein to refer to biological molecules comprising a plurality of nucleotides. Exemplary polynucleotides include deoxyribonucleic acids, ribonucleic acids, and synthetic analogues thereof, including peptide nucleic acids.

II. Methods of Detection

Described herein are methods for detecting the presence or absence of at least one polynucleotide analyte in a sample. Detection methods provided herein may use an amplification or polymerization technique (e.g., polymerase chain reaction (PCR) or PCR process) to incorporate chromophores directly onto the product (e.g., analyte) templates. An exemplary detection method is shown in FIG. 1, in which a pair of primers, each attached to either a fluorophore or a quencher at its 5' end respectively, is used to detect an analyte by amplification or polymerization process. In some cases, a first signal is measured prior to the start of the amplification or polymerization reaction. During the initial amplification or polymerization cycle, a duplex DNA separates, allowing primers to bind to specific regions of the individual template strands (FIGS. 1A-1C). A polymerase (e.g. Taq polymerase) can be used to extend the primers along the template strand (FIG. 1D). In some cases, a second signal can be measured after the initial cycle. In some cases, a change in signal is not observed after the initial cycle (FIG. 1E) since a single chromophore is incorporated into the template. In some cases, upon completion of a second cycle, a change in signal can be observed due to the incorporation of both chromophores in the synthesized template (FIG. 1F). In some cases, a second signal can be measured after the second cycle. In some cases, the first and second signals are used to detect the presence or absence of the amplified product (e.g. the polynucleotide analyte). In some cases, a change is observed between the first and second signal. In some cases, the change in signal indicates the presence of the amplified product (e.g. the polynucleotide analyte).

In some cases, the change in signal is an increase in signal (e.g., an increased quenching of fluorescence when a fluorophore and quencher are incorporated into the amplified product). In some cases, the change in signal is a decrease in signal (e.g., a decrease in fluorescence intensity). In some cases, an increase in signal indicates a presence of the product or analyte. In some cases, a decrease in signal indicates a presence of the product or analyte. In some cases, the lack of a change in signal (e.g., no significant change in fluorescence intensity) indicates the absence of the product or analyte. In some cases, a denaturation signal is measured before, during, or after the denaturation step. In some cases, an annealing signal is measured before, during, or after the annealing step. In some cases, an annealing signal is measured before, during, or after the extension step. In some cases, the denaturation signal is compared with a reference signal or reference signal range as described elsewhere herein to determine if the amplification or polymerization reaction has proceeded reliably or correctly. In some cases, when the denaturation signal falls outside of the reference signal range, it can indicate that the reaction has failed. In some cases, when the denaturation signal falls within the reference signal range, the denaturation signal can be used to normalize the annealing signal. In some cases, the denaturation signal from each cycle can be used for a cycle-by-cycle normalization of the annealing signals (e.g. chopper stabilization). In some cases, the change in annealing signals is referred to as a relative quantitation of signals. In some cases, the signal is not limited to a signal generated by a fluorophore and quencher pair. In some cases, the signal can be generated by different chromophores.

In some cases, the change in signal can be defined by a percentage change. In some cases, the change in signal can be about 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, 1000%, or more. In some cases, the change in signal can be greater than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, or 1000%. In some cases, the change in signal can be less than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, or 1000%. In some cases, the change in signal can be about 50%.

Various combinations of oligonucleotides (e.g. primers and/or probes) can be used to detect an analyte. In some cases, a primer is used with a probe or a plurality of probes. In some cases, a plurality of primers is used with a plurality of probes. In some cases, a plurality of primers is used with a single probe. In some cases, a primer pair is used to detect an analyte. In some cases, a primer pair is used to detect multiple analytes. In some cases, multiple primer pairs are used to detect an analyte. In some cases, a primer and a probe is used to detect an analyte. In some cases, a primer and a probe is used to detect multiple analytes. In some cases, a combination of primers and probes is used to detect an analyte. In some cases, a combination of primers and probes is used to detect multiple analytes. In some cases, a probe is used to detect an analyte. In some cases, a probe is used to detect multiple analytes. In some cases, multiple probes are used to detect an analyte.

In some cases, at least one chromophore (e.g. fluorophore, quencher, intercalating dye) is used to detect an analyte. In some cases, a chromophore pair (e.g. fluorophore/quencher pairs) is used to detect an analyte. In some cases, a single chromophore pair is used to detect an analyte. In some cases, a single chromophore pair is used to detect multiple analytes. In some cases, multiple chromophore pairs are used to detect an analyte. In some cases, a chromophore pair comprises a first chromophore and a second chromophore. In some cases, each primer in a primer pair comprises either a first chromophore (e.g. a fluorophore) or a second chromophore (e.g. a quencher). In some cases, each primer in the primer pair does not comprise both first and second chromophores. In some cases, a chromophore pair is not used to detect an analyte. In some cases, a chromophore is not used to detect an analyte. In some cases, a chromophore is an intercalating dye. In some cases, an intercalating dye is not used to detect an analyte. In some cases, the first chromophore and the second chromophore are the same.

In some cases, a plurality of primers is used in the detection methods. In some cases, a primer is used with an oligonucleotide (e.g. a probe) or a plurality of oligonucleotides (e.g. a plurality of probes). In some cases, a primer is used with a probe or a plurality of probes. In some cases, a plurality of primers is used with a plurality of probes. In some cases, a plurality of primers is used with a single probe. In some cases, the number of primers used equals the number of probes used in the detection methods. In some cases, the primer is not attached to the oligonucleotide.

In some cases, a probe is not used in the detection methods. In some cases, a probe with chromophores attached is not used in the detection methods. In some cases, a probe (such as a self-quenching probe) with a fluorophore and quencher pair attached is not used in the detection methods. In some cases, a probe with a fluorophore attached at its 5' end and a quencher attached at its 3' end is not used in the detection methods.

In some cases, the method is used with a second method. In some cases, the second method is an amplification or polymerization method, an electrophoresis (e.g. gel electrophoresis, capillary electrophoresis), a mass spectroscopy method, a chromatography method or an assay (e.g. in vitro cell based assay). In some cases, the amplification or polymerization method is an isothermal reaction method or a polymerase chain reaction method. In some cases, the polymerase chain reaction process is a multiplex-PCR, a quantitative PCR (qPCR), an end point PCR or a digital PCR (e.g. droplet digital PCR) process. In some cases, the polymerase chain reaction is a droplet digital PCR. In some cases, the second method is a droplet digital PCR method. In some cases, the second method is an electrophoresis method (e.g. a gel electrophoresis method for DNA sequencing). In some cases, the method is used in combination with a second and a third method. In some cases, the third method is an amplification or polymerization method, an electrophoresis (e.g. gel electrophoresis, capillary electrophoresis), a mass spectroscopy method, a chromatography method or an assay (e.g. in vitro cell based assay). In some cases, the method is used without a second or a third method. In some cases, the method is used without a second method. In some cases, the method is used without an electrophoresis method. In some cases, the method is used without a sequencing method.

A. Detection of Analytes from Intensity-Length Relationship

Described herein is a method of detecting the presence of one or more analytes in a sample. Methods provided herein involve, e.g., the measurement of the change in signal intensity when at least two chromophores interact with each other. For example, in the case of a fluorophore and quencher interaction, the further the fluorophore is from the quencher, the brighter the fluorescence signature of a particular nucleic acid analyte will typically be. So long that the analyte lengths are small, the persistence length of the nucleic acid analyte typically determines the intensity of fluorescence. For example, for a given fluorophore-quencher pair, the intensity of the fluorescence can be correlated with the persistence length. Further, the intensity of fluorescence often indicative of an energy transfer between the fluorophore and the quencher. The efficiency of this energy transfer is described by the following equation:

$$E = \frac{1}{1 + (r/R_0)^6} \quad (1)$$

where r is the distance between the fluorophore and the quencher (FIG. 2) and $R_0$ is a constant related to each fluorophore/quencher pair where it can be calculated from certain parameters of the absorption and emission spectra of each chromophore. (See Biophysical Chemistry, D. Freifelder, ed., W.H. Freeman and Company, San Francisco (1976) at page 426-28). Further, $R_0$ is described by the following equation:

$$R_0^6 = \frac{9 Q_0 (\ln 10) \kappa^2 J}{128 \pi^5 n^4 N_A} \quad (2)$$

where $Q_0$ is the fluorescence quantum yield of the donor in the absence of the acceptor, $\kappa^2$ is the dipole orientation factor, n is the refractive index of the medium, $N_A$ is Avogadro's number and J is the spectral overlap integral (FIG. 2).

Therefore, the changes in fluorescence signal typically vary with the length of the synthesized strand. In some cases, a decrease in fluorescence signal is inversely proportional with the length of the synthesized strand. Utilizing this relationship, the presence of an analyte can be detected based on the signal correlated with its length. For example, a set of fluorescence signal ladders reminiscent of molecular weight ladders based on DNA length can be established as a control. In a sample, multiple pairs of primers attached with the same fluorophore/quencher pair are amplified. Upon completion of the amplification or polymerization process, the observed signals can be correlated with the controls, thereby detecting the presence or absence of a particular analyte. In some cases, the presence or absence of a particular analyte can be monitored throughout the amplification or polymerization process, by taking measurements during each amplification or polymerization cycle and comparing with the control ladder. In some cases, the ladder comprises a plurality of signals. In some cases, the plurality of signals generates multiple curves. In some cases, the ladder is represented by a plurality of curves. In some cases, the ladder comprises multiple sets of endpoint fluorescence. In some cases, the ladder comprises multiple sets of initial and end point fluorescence. In some cases, each step of the ladder comprises a plurality of signals. In some cases, the plurality of signals generates a curve. In some cases, each step of the ladder is represented by a curve. In some cases, each step of the ladder comprises an endpoint fluorescence measurement. In some cases, each step of the ladder comprises a set of initial and endpoint fluorescence measurements. In some cases, each step of the ladder comprises an initial and endpoint fluorescence. In some cases, the curve represents a signature profile of an analyte based on its length. In some cases, the endpoint fluorescence represents a signature profile of an analyte based on its length. In some cases, the set of initial and endpoint fluorescence represents a signature profile of an analyte based on its length. In some cases, the initial and endpoint fluorescence represents a signature profile of an analyte based on its length. In some cases, each step of the ladder generates a signature profile of an analyte based on its length. In some cases, the ladder comprises multiple steps or multiple signature profiles of analytes. In some cases, the ladder comprises a single step or a single signature profile of an analyte. In some cases, the ladder comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or more steps. In some cases, the ladder comprises more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 steps. In some cases, the ladder comprises less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 steps. In some cases, multiple analytes are detected by a single fluorophore/quencher pair. In some cases, a single analyte is detected by a single fluorophore/quencher pair. In some cases, the signal is not limited to a signal generated by a fluorophore and quencher pair. In some cases, the signal can be generated by different chromophores.

B. Detection of Genetic Variations

Disclosed herein is a method of determining the presence or absence of a genetic variation, e.g., based on the change in signal due, e.g., to a disruption in the electron transport mechanism described herein. Genetic variations include deletion and insertion of one or more nucleotides, translocations of different nucleotide occurrences (e.g. single point mutations such as SNPs or a base-pair substitution), or variations in the number of multiple nucleotide repetitions. For example, to detect the presence of a single deletion or alteration (e.g. a SNP) in a template (e.g. an analyte), a first primer is designed to hybridize to a region comprising the deletion. A second primer comprises a sequence complementary to the region of the analyte about less than 500 bp away from the first primer. Upon amplification or polymerization, a change in signal is observed. However, since a kink is present in the product template, an inefficient electron transport results in a decrease in the change of signal, e.g., when compared to the change in signal observed for an analyte without the genetic variation.

In some cases, the genetic variation detected is a different nucleotide occurrence in the analyte. In some cases, the different nucleotide occurrence is a single-nucleotide polymorphism (SNP). A SNP is a DNA sequence variation that occurs when a single nucleotide (e.g. A, T, C or G) in the genome is altered. In some cases, this alteration leads to either a presence of disease or is associated with (or a marker for) the presence of a disease or diseases. For example, a single nucleotide mutation from GAG to GTG in the β-globin gene that encodes haemoglobin results in development of sickle-cell anaemia.

In general, each individual has many SNPs that create a unique human DNA pattern. In some cases, a SNP is a common SNP or a rare SNP. In some cases, a SNP is a common SNP. In some cases, a common SNP has a minor allele frequency of about 1%, 2%, 3%, 4%, 5%, 6%, 7%, 8%, 9%, 10%, 11%, 12%, 13%, 14%, 15%, 16%, 17%, 18%, 19%, 20%, or more. In some cases, a common SNP has a minor allele frequency of greater than 1%, 2%, 3%, 4%, 5%, 6%, 7%, 8%, 9%, 10%, 11%, 12%, 13%, 14%, 15%, 16%, 17%, 18%, 19%, or 20%. In some cases, a common SNP has a minor allele frequency of less than 1%, 2%, 3%, 4%, 5%, 6%, 7%, 8%, 9%, 10%, 11%, 12%, 13%, 14%, 15%, 16%, 17%, 18%, 19%, or 20%. In some cases, a SNP is a rare SNP. In some cases, a rare SNP has a minor allele frequency of about 1%, 2%, 3%, 4%, 5%, 6%, 7%, 8%, 9%, 10%, 11%, 12%, 13%, 14%, 15%, 16%, 17%, 18%, 19%, 20%, or more. In some cases, a rare SNP has a minor allele frequency of greater than 1%, 2%, 3%, 4%, 5%, 6%, 7%, 8%, 9%, 10%, 11%, 12%, 13%, 14%, 15%, 16%, 17%, 18%, 19%, or 20%. In some cases, a rare SNP has a minor allele frequency of less than 1%, 2%, 3%, 4%, 5%, 6%, 7%, 8%, 9%, 10%, 11%, 12%, 13%, 14%, 15%, 16%, 17%, 18%, 19%, or 20%.

In some cases, provided herein is a method to detect the presence of a SNP. In some cases, the method described herein is used to detect the presence of a common SNP. In some cases, the method described herein is used to detect the presence of a rare SNP. In some cases, the method described herein is used to detect the presence of a combination of common and rare SNPs.

In some cases, the method described herein is used to detect the presence of SNP in a sample. In some cases, the method described herein is used to detect multiple SNPs in a sample. In some cases, the method described herein is used to detect multiple common SNPs in a sample. In some cases, the method described herein is used to detect multiple rare SNPs in a sample. In some cases, the method described herein is used to detect a combination of common and rare SNPs in a sample. In some cases, the method described herein is used to detect a single SNP in a sample. In some cases, the method described herein is used to detect a single common SNP in a sample. In some cases, the method described herein is used to detect a single rare SNP in a sample.

In some cases, a plurality of SNPs is detected in a sample using a single chromophore pair (e.g. fluorophore/quencher pair). In some cases, the plurality of SNPs can be detected based in part on the length of each analyte containing a specific SNP. In some cases, a set of fluorescence ladder comprising SNP analytes (an analyte containing at least one SNP) of known length as described herein is generated. In some cases, the set of fluorescence ladder is used as a control. In some cases, the presence or absence of a particular SNP analyte can be determined by taking measurements during the amplification or polymerization reaction and comparing with the control ladder. In some cases, the presence or absence of a particular SNP analyte can be monitored throughout the amplification or polymerization process, by taking measurements during each amplification or polymerization cycle and comparing with the control ladder. In some cases, a plurality of SNPs is detected in a sample using a relative quantification method.

In some cases, the presence of SNPs correlates directly with the development of a disease. In some cases, the presence of SNPs increases the chances of developing a disease. In some cases, the disease comprises a genetic disorder, an autoimmune disease, a neurological disease, a cardiovascular disease and cancer.

C. Monitoring an Amplification or Polymerization Reaction

Disclosed herein is a method for detecting a change in signal generated by a set of chromophores for monitoring a reaction. In some cases, the method described herein can be used to monitor the progress of a PCR reaction. For example, at cycle 1, a set of fluorescence signals are measured, one measurement at the denaturing step and one measurement at the annealing step. During cycle 2, a second set of fluorescence signals are measured at the denaturing and annealing steps. A change in fluorescence between the signals taken at the two annealing step indicate an occurrence of a PCR reaction, while the signals taken during the denaturing steps are used both as a control and a normalization parameter.

In some cases, signals measured from the annealing steps are used to monitor the progress of a reaction. In some cases, the change in signal from two annealing steps is measured. The change in signal can be, e.g., an increase in signal or a decrease in signal. In some cases, the change in signal is defined by a percentage change. In some cases, the change in signal can be about 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, 1000% or more. In some cases, the change in signal can be greater than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900% or 1000%. In some cases, the change in signal can be less than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900% or 1000%. In some cases, signals are measured before, during or after the annealing step.

In some cases, signals measured from the extension steps are used to monitor the progress of a reaction. In some cases, the change in signal from two extension steps is measured. The change in signal can be, e.g., an increase in signal or a decrease in signal. In some cases, the change in signal is defined by a percentage change. In some cases, the change in signal can be about 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, 1000%, or more. In some cases, the change in signal can be greater than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, or 1000%. In some cases, the change in signal can be less than 0.001%, 0.01%, 0.1%, 1%, 10%, 20%, 30%, 40%, 50%, 60%, 70%, 80%, 90%, 100%, 200%, 300%, 400%, 500%, 600%, 700%, 800%, 900%, or 1000%. In some cases, the signals are measured before, during or after the extension step.

In some cases, the signals measured from the denaturing steps are used to monitor the progress of a reaction. In some cases, the denaturation signals are compared with a reference signal or reference signal range. As described elsewhere herein, when a denaturation signal is outside of the reference signal range, the denaturation signals can indicate that the reaction has failed. In some cases, when the denaturation signal is within the reference signal range, the denaturation signals can indicate that the reaction has succeeded. In some cases, the denaturation signals serve as a control for each amplification or polymerization cycle. In some cases, the denaturation signal is used for normalization during an amplification or polymerization experiment. As described elsewhere herein, when the denaturation signal is within the reference signal range, the denaturation signal from each amplification or polymerization cycle can be used to normalize the annealing signal from that cycle. In some cases, the denaturation signals are used for cycle-by-cycle self-normalization of a reaction. In some cases, signals are measured before, during or after the denaturation step.

In some cases, multiple reactions are monitored. In some cases, multiple reactions from a single sample are monitored. In some cases, multiple reactions from multiple samples are monitored. In some cases, a single reaction is monitored. In some cases, a single reaction from a single sample is monitored. In some cases, the reaction is used to detect the presence of a genetic variation. In some cases, the reaction for detecting the presence of a genetic variation is monitored. In some cases, the reaction is used to detect the presence of a SNP. In some cases, the reaction for detecting the presence of a SNP is monitored. In some cases, multiple oligonucleotides (e.g. primers and/or probes) are used. In some cases, multiple primers are used. In some cases, multiple probes are used. In some cases, the number of primers equals the number of probes.

D. Detection of Morphological Change

Disclosed herein is a method for detecting or monitoring a morphological change in an analyte based on changes in signals. In some cases, an analyte is a protein, a polynucleotide, a lipid, a carbohydrate or an antibody. In some cases, an analyte is a polynucleotide. In some cases, the polynucleotide is a DNA or a RNA. In some cases, DNA and RNA can adopt different conformations such as a hairpin, tetraloop or pseudoknot. For example, to detect the different morphological state of a DNA containing a hairpin, a fluorophore/quencher pair can be attached to the respective stem of the hairpin. Since the fluorophore is in close proximity to the quencher, a signal may not be observed. As the temperature increases, the DNA hairpin unwinds and a fluorescence signal may be observed. In some cases, multiple signals are measured as the DNA unwinds. In some cases, only an initial and an end-point signals are measured as the DNA unwinds. In some cases, the multiple signals can generate a curve. In some cases, the multiple signals are used to generate a signature profile of a DNA containing a hairpin. In some cases, the signature profile is a curve. In some cases, an initial and an end-point signals are used to generate a signature profile. In some cases, the signature profile obtained from the DNA denaturation study is used as a control to detect the presence of a hairpin in a target DNA. In some cases, the method described herein is used to monitor the stability of a DNA or RNA conformation after introduction of addition, deletion, substitution or base modifications (e.g. unnatural bases) within the DNA or RNA. In some cases, the stability is affected by external factors. In some cases, the external factors include pH, organic or inorganic agents (e.g. salt, intercalating dye) or additional analytes. In some cases, the additional analyte is a DNA, RNA, protein or an antibody. In some cases, the method described herein is used to monitor the stability of a DNA or RNA conformation after introduction of the external factors.

In some cases, the method described herein is used to monitor a morphological change of a protein. For example, a protein residing in a native state can be a folded protein, a partially folded protein or a disordered protein. Folding or unfolding occurs due to the presence of binding partners, organic or inorganic agents, pH, and temperature. For a folded protein, an increase in temperature induces the protein to undergo an unfolding state. By attaching proteins to a plurality of fluorophores and/or quenchers, a fluorescence signal can be measured with each iterative temperature increase and can be compared to the signals taken at its native state. In some cases, multiple signals are measured as the protein unfolds. In some cases, only an initial and an end-point signals are measured as the protein unfolds. In some cases, multiple signals can generate a curve. In some cases, multiple signals are used to generate a signature profile of the protein. In some cases, the signature profile is a curve. In some cases, an initial and an end-point signals are used to generate a signature profile. In some cases, the signature profile obtained from the protein unfolding study is used as a control to detect the morphology of proteins containing similar folds. In some cases, the method described herein is used to monitor the stability of a protein. In some cases, unfolding of the protein can be induced upon addition of an external factor. In some cases, the external factors include pH, organic or inorganic agents (e.g. salt, intercalating dye) or additional analytes. In some cases, the additional analyte is a DNA, RNA, protein, or an antibody.

In some cases, the method described herein is used to monitor the morphology of an analyte-analyte interaction such as a protein-protein, protein-antibody or protein-polynucleotide (e.g. protein-DNA or protein-RNA) interactions. For example, during a protein-DNA interaction, a protein can adopt a different conformation upon binding of the DNA. In some cases, the change in signal associated with binding can be used to compare with the protein at its apo or unbound state. In some cases, multiple signals are measured as the protein-DNA complex forms. In some cases, only an initial and an end-point signals are measured as the complex forms. In some cases, the multiple signals can generate a curve. In some cases, the multiple signals are used to generate a signature profile of the protein. In some cases, the signature profile is a curve. In some cases, an initial and an end-point signals are used to generate a signature profile. In some cases, the signature profile obtained from the protein-DNA study is used as a control to detect the formation of protein complex with additional DNAs. In some cases, the methods described herein can monitor the stability of the protein complex with addition of another external factor. In some cases, the methods described herein can be used to monitor the morphological change of an analyte with multiple binding partners.

III. Multiplex Detection

Disclosed herein are examples of determining the presence of a plurality of analytes using a plurality of chromophores to indicate the presence or absence of these analytes. For example, a multiplex detection method can combines the use of color, signal, and/or mathematical strategies to circumvent degeneracy and ensure an infinite number of unique codes that can be unambiguously decoded in any combination of occurrences. For example, in detecting a sample containing four analytes, each analyte can be assigned a fluorophore (blue, green, yellow, or red) and a quencher attached to analyte-specific oligonucleotides (e.g., a forward PCR primer and a reverse PCR primer). Upon amplification or polymerization, the presence or absence of an analyte is determined based on the presence or absence of a signal in that particular color.

In some cases, multiple color codes are generated using a plurality of chromophores. In some cases, multiple color codes are generated using a plurality of fluorophores and quenchers. In some cases, multiple color codes are generated using combinations of fluorophore/quencher pairs. In some cases, multiple chromophores are assigned to multiple analytes. In some cases, a single chromophore is assigned to multiple analytes. In some cases, a single chromophore is assigned to one analyte.

In some cases, one color code or chromophore combination is assigned to one analyte. In some cases, one color code or chromophore combination is assigned to multiple analytes (e.g., to discriminate multiple analytes of varying lengths in a single detection reaction). In some cases, one color code or chromophore combination is assigned to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000, or 100,000 analytes. In some cases, multiple color codes or chromophore combinations are assigned to one or more analytes. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000, or 100,000 color codes or chromophore combinations are assigned to one or more analytes (e.g. 1, 5, 10, 100, 500, 10,000 analytes). In some cases, at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000, or 100,000 color codes or chromophore combinations are assigned to one or more analytes (e.g. 1, 5, 10, 100, 500, 10,000 analytes).

In some cases, one color is assigned as a control. In some cases, the control is a positive control or a negative control.

A. Multiplex Detection for Genetic Variation

In some cases, the methods disclosed herein can be used to detect the presence of multiple genetic variations (e.g., SNPs). In some cases, an analyte contains a plurality of genetic variations. In some cases, an analyte contains one genetic variation. In some cases, one color is assigned to one genetic variation. In some cases, a sample contains a plurality of genetic variations, wherein a color code or chromophore combination is assigned to each genetic variation. In some cases, a sample contains one genetic variation.

B. Multiplex Detection for SNP

In some cases, disclosed herein are methods of detecting the presence or absence of a SNP in an analyte. In some cases, an analyte contains a plurality of SNPs. In some cases, an analyte contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or more SNPs. In some cases, an analyte contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 SNPs. In some cases, an analyte contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 SNPs. In some cases, an analyte contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or more common SNPs. In some cases, an analyte contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 common SNPs. In some cases, an analyte contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 common SNPs. In some cases, an analyte contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, or more rare SNPs. In some cases, an analyte contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 rare SNPs. In some cases, an analyte contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, or 500 rare SNPs.

In some cases, a sample contains a plurality of analytes. In some cases, multiple SNPs are detected from a plurality of analytes in the sample. In some cases, multiple common SNPs are detected from a plurality of analytes in the sample. In some cases, multiple rare SNPs are detected from a plurality of analytes in the sample. In some cases, multiple SNPs are detected from an analyte in the sample. In some cases, multiple common SNPs are detected from an analyte in the sample. In some cases, multiple rare SNPs are detected from an analyte in the sample. In some cases, one SNP is detected from an analyte in the sample. In some cases, one common SNP is detected from an analyte in the sample. In some cases, one rare SNP is detected from an analyte in the sample. In some cases, one SNP is detected in the sample. In some cases, one common SNP is detected in the sample. In some cases, one rare SNP is detected in the sample.

In some cases, a sample contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more SNPs. In some cases, a sample contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more SNPs. In some cases, a sample contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more SNPs. In some cases, a sample contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more common SNPs. In some cases, a sample contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more common SNPs. In some cases, a sample contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more common SNPs. In some cases, a sample contains 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more rare SNPs. In some cases, a sample contains at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more rare SNPs. In some cases, a sample contains no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more rare SNPs.

In some cases, the methods described herein comprise detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more SNPs. In some cases, the methods described herein comprise detecting at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more SNPs. In some cases, the methods described herein comprise detecting no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more SNPs. In some cases, the methods described herein comprise detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more common SNPs. In some cases, the methods described herein comprise detecting at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more common SNPs. In some cases, the methods described herein comprise detecting no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more common SNPs. In some cases, the methods described herein comprise detecting 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more rare SNPs. In some cases, the methods described herein comprise detecting at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more rare SNPs. In some cases, the methods described herein comprise detecting no more than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 5000, 10,000, 50,000, 100,000, or more rare SNPs.

In some cases, the method of detection utilizes an amplification or polymerization method. In some cases, an amplification or polymerization method (or process) comprises a polymerase chain reaction (PCR) method and an isothermal reaction method. In some cases, a PCR reaction process comprises a multiplex PCR, a real-time PCR, a quantitative PCR and a digital PCR (e.g. droplet digital PCR) process. In some cases, the method of detection utilizes a quantitative PCR method. In some cases, the quantitative PCR method is used in combination with a second method. In some cases, the second method is a digital PCR method. In some cases, the second method is a droplet digital PCR method.

In some cases, a signature profile is used to detect the presence of a SNP. In some cases, a signature profile is used to pinpoint the nucleotide mutation. In some cases, a signature profile is unique for each nucleotide mismatch, UU, UT, UG, UC, UA, AA, TT, GG, CC, AG, AC, TC, TC, and distinct from the wild-type. In some cases, a signature profile of a nucleotide mismatch is compared to that of a wild-type. In some cases, the signature profile of a SNP is compared to that of a wild-type. In some cases, a fluorescence signal of a SNP is compared to a fluorescence signal of a wild-type. In some cases, a change in fluorescence signal is detected between the signals of a SNP and a wild-type. In some cases, the change in signal can be calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, a change in signal is detected between the fluorescence signals of an AG mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, a change in signal is detected between the fluorescence signals of an AC mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, a change in signal is detected between the fluorescence signals of a TG mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, a change in signal is detected between the fluorescence signals of a TC mismatch and a wild-type. In some cases, the change in signal is calculated as a percentage. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, or 100%.

In some cases, a pair of primers is utilized to detect a SNP. In some cases, the first primer comprises a sequence encoding the SNP. In some cases, the first primer hybridizes to a region of the analyte encoding the SNP. In some cases, the second primer comprises a sequence not encoding the SNP. In some cases, the second primer comprises a sequence complementary to a region of the analyte not encoding the SNP. In some cases, the first primer encodes a region on the analyte greater than 500 base pairs apart from a region of the analyte encoded by the second primer. In some cases, the first primer encodes a region on the analyte less than 500 base pairs apart from a region encoded by the second primer. In some cases, the first primer encodes a region on the analyte less than 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20 base pairs apart from a region encoded by the second primer. In some cases, the first primer encodes a region on the analyte no more than 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20 base pairs apart from a region encoded by the second primer. In some cases, the first primer encodes a region on the analyte about 490, 480, 470, 460, 450, 440, 430, 420, 410, 400, 390, 380, 370, 360, 350, 340, 330, 320, 310, 300, 290, 280, 270, 260, 250, 240, 230, 220, 210, 200, 195, 190, 185, 180, 175, 170, 165, 160, 155, 150, 145, 140, 135, 130, 125, 120, 115, 110, 105, 100, 99, 98, 97, 96, 95, 94, 93, 92, 91, 90, 89, 88, 87, 86, 85, 84, 83, 82, 81, 80, 79, 78, 77, 76, 75, 74, 73, 72, 71, 70, 69, 68, 67, 66, 65, 64, 63, 62, 61, 60, 59, 58, 57, 56, 55, 54, 53, 52, 51, 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20 base pairs apart from a region encoded by the second primer.

IV. Analytes

An analyte may be any suitable analyte that can be analyzed using the methods and compositions of the present disclosure, where the analyte is capable of interacting with a reagent (e.g., an oligonucleotide such as a primer or probe attached to a chromophore) in order to generate a signal that can be measured. An analyte may be naturally-occurring or synthetic. An analyte may be present in a sample obtained using any methods known in the art. In some cases, a sample may be processed before analyzing it for an analyte. The methods and compositions presented in this disclosure may be used in solution phase assays, without the need for particles (such as beads) or a solid support.

In some cases, an analyte may be a polynucleotide, such as DNA, RNA, peptide nucleic acids, and any hybrid thereof, where the polynucleotide contains any combination of deoxyribo- and/or ribo-nucleotides. Polynucleotides may be single stranded or double stranded, or contain portions of both double stranded or single stranded sequence. Polynucleotides may contain any combination of nucleotides or bases, including, for example, uracil, adenine, thymine, cytosine, guanine, inosine, xanthine, hypoxanthine, isocytosine, isoguanine, and any nucleotide derivative thereof. As used herein, the term "nucleotide" may include nucleotides and nucleosides, as well as nucleoside and nucleotide analogs, and modified nucleotides, including both synthetic and naturally occurring species. Polynucleotides may be any suitable polynucleotide for which one or more reagents as described herein may be produced, including but not limited to cDNA, mitochondrial DNA (mtDNA), messenger RNA (mRNA), ribosomal RNA (rRNA), transfer RNA (tRNA), nuclear RNA (nRNA), small interfering RNA (siRNA), small nuclear RNA (snRNA), small nucleolar RNA (snoRNA), small Cajal body-specific RNA (scaRNA), microRNA (miRNA), double stranded (dsRNA), ribozyme, riboswitch, or viral RNA. Polynucleotides may be contained within any suitable vector, such as a plasmid, cosmid, fragment, chromosome, or genome. In some cases, the analyte is referred to as a polynucleotide analyte. In some cases, the analyte is referred to as a nucleic acid analyte. In some cases, the analyte is referred to as a nucleic acid target.

Genomic DNA may be obtained from naturally occurring or genetically modified organisms or from artificially or synthetically created genomes. Analytes comprising genomic DNA may be obtained from any source and using any methods known in the art. For example, genomic DNA may be isolated with or without amplification or polymerization. Amplification or polymerization may include PCR amplification, multiple displacement amplification (MDA), rolling circle amplification and other amplification or polymerization methods. Genomic DNA may also be obtained by cloning or recombinant methods, such as those involving plasmids and artificial chromosomes or other conventional methods (see Sambrook and Russell, *Molecular Cloning: A Laboratory Manual*, cited supra.) Polynucleotides may be isolated using other methods known in the art, for example as disclosed in *Genome Analysis: A Laboratory Manual Series* (Vols. I-IV) or *Molecular Cloning: A Laboratory Manual*. If the isolated polynucleotide is an mRNA, it may be reverse transcribed into cDNA using conventional techniques, as described in Sambrook and Russell, *Molecular Cloning: A Laboratory Manual*, cited supra.

An analyte may be a protein, polypeptide, lipid, carbohydrate, sugar, small molecule, or any other suitable molecule that can be detected with the methods and compositions provided herein. An analyte may be an enzyme or other protein. An analyte may be a drug or metabolite (e.g. anti-cancer drug, chemotherapeutic drug, anti-viral drug, antibiotic drug, or biologic). An analyte may be any molecule, such as a co-factor, receptor, receptor ligand, hormone, cytokine, blood factor, antigen, steroid, or antibody.

An analyte may be any molecule from any pathogen, such as a virus, bacteria, parasite, fungus, archaea or prion (e.g., PrP$^{Sc}$). Exemplary viruses include those from the families Adenoviridae, Flaviviridae, Hepadnaviridae, Herpesviridae, Orthomyxoviridae, Papovaviridae, Paramyxoviridae, Picornaviridae, Polyomavirus, Retroviridae, Rhabdoviridae, and Togaviridae. Specific examples of viruses include adenovirus, astrovirus, bocavirus, BK virus, coxsackievirus, cytomegalovirus, dengue virus, Ebola virus, enterovirus, Epstein-Barr virus, feline leukemia virus, hepatitis virus, hepatitis A virus, hepatitis B virus, hepatitis C virus, hepatitis D virus, hepatitis E virus, herpes simplex virus (HSV), HSV type 1, HSV type 2, human immunodeficiency virus (HIV), HIV type 1, HIV type 2, human papilloma virus (HPV), HPV type 1, HPV type 2, HPV type 3, HPV type 4, HPV type 6, HPV type 10, HPV type 11, HPV type 16, HPV type 18, HPV type 26, HPV type 27, HPV type 28, HPV type 29, HPV type 30, HPV type 31, HPV type 33, HPV type 34, HPV type 35, HPV type 39, HPV type 40, HPV type 41, HPV type 42, HPV type 43, HPV type 44, HPV type 45, HPV type 49, HPV type 51, HPV type 52, HPV type 54, HPV type 55, HPV type 56, HPV type 57, HPV type 58, HPV type 59, HPV type 68, HPV type 69, influenza type A virus, influenza type B virus, JC virus, Marburg virus, measles virus, metapneumovirus, mumps virus, Norwalk virus, parovirus, polio virus, rabies virus, respiratory syncytial virus including type A and type B, retrovirus, rhinovirus, rotavirus, Rubella virus, smallpox virus, vaccinia virus, West Nile virus, yellow fever virus, and human parainfluenza virus type 3.

Exemplary bacteria include those from the genera *Bordetella, Borrelia, Brucella, Campylobacter, Chlamydia, Clostridium, Corynebacterium, Enterococcus, Escherichia, Francisella, Haemophilus, Helicobacter, Legionella, Leptospira, Listeria, Mycobacterium, Mycoplasma, Neisseria, Pseudomonas, Rickettsia, Salmonella, Shigella, Staphylococcus, Streptococcus, Treponema, Vibrio,* and *Yersinia.* Specific examples of bacteria include *Bordetella par apertussis, Bordetella pertussis, Borrelia burgdorferi, Brucella abortus, Brucella canis, Brucella melitensis, Brucella suis, Campylobacter jejuni, Chlamydia pneumoniae, Chlamydia psittaci, Chlamydia trachomatix, Clostridium botulinum, Clostridium difficile, Clostridium perfringens, Clostridium tetani, Corynebacterium diphtherias, Enterococcus faecalis, Enterococcus faecium, Escherichia coli, Francisella tularensis, Haemophilus influenzae, Helicobacter pylori, Legionella pneumophila, Leptospira interrogans, Listeria monocytogenes, Mycobacterium leprae, Mycobacterium tuberculosis, Mycobacterium ulcerans, Mycoplasma pneumoniae, Neisseria gonorrhoeae, Neisseria meningitidis, Pseudomonas aeruginosa, Rickettsia rickettsii, Salmonella choleraesuis, Salmonella dublin, Salmonella enteritidis, Salmonella typhi, Salmonella typhimurium, Shigella sonnei, Staphylococcus aureus, Staphylococcus epidermidis, Staphylococcus saprophyticus, Streptococcus agalactiae, Streptococcus pneumoniae, Streptococcus pyogenes, Treponema pallidum, Vibrio cholerae, Yersinia pestis,* and *Yersinia enterocolitica.*

Exemplary parasites include those from the genera *Acanthamoeba, Babesia, Balamuthia, Balantidium, Blasocystis, Cryptosporidium, Dientamoeba, Entamoeba, Giardia, Isospora, Leishmania, Naegleria, Pediculus, Plasmodium, Rhinosporidium, Sarcocystis, Schistosoma, Toxoplasma, Trichomonas,* and *Trypanosoma.* Specific examples of parasites include *Babesia divergens, Babesia bigemina, Babesia equi, Babesia microfti, Babesia duncani, Balamuthia mandrillaris, Balantidium coli, Dientamoeba fragilis, Entamoeba histolytica, Giardia lamblia, Isospora belli, Naegleria fowleri, Pediculus humanus, Plasmodium falciparum, Plasmodium knowlesi, Plasmodium malariae, Plasmodium ovale, Plasmodium vivax, Rhinosporidium seeberi, Sarcocystis bovihominis, Sarcocystis suihominis, Schistosoma mansoni, Toxoplasma gondii, Trichomonas vaginalis, Trypanosoma brucei,* and *Trypansoma cruzi.*

Exemplary fungi include those from the genera *Apophysomyces, Aspergillus, Blastomyces, Candida, Cladosporium, Coddidioides, Cryptococcos, Exserohilum, Fusarium, Histoplasma, Pichia, Pneumocystis, Saccharomyces, Sporothrix, Stachybotrys,* and *Trichophyton.* Specific examples of fungi include *Aspergillus fumigatus, Aspergillus flavus, Aspergillus clavatus, Blastomyces dermatitidis, Candida albicans, Coccidioides immitis, Crytpococcus neoformans, Exserohilum rostratum, Fusarium verticillioides, Histoplasma capsulatum, Pneumocystis jirovecii, Sporothrix schenckii, Stachybotrys chartarum,* and *Trichophyton mentagrophytes.*

Exemplary archaea include those from the genera *Acidilobus, Acidococcus, Aeropyrum, Archaeoglobus, Caldisphaera, Caldococcus, Cenarchaeum, Desulfurococcus, Geogemma, Geoglubus, Haladaptatus, Halomicrobium, Hyperthermus, Ignicoccus, Ignisphaera, Methanobacterium, Natronococcus, Nitrosopumilus, Picrophilus, Pyrodictium, Pyrolobus, Staphylothermus, Stetteria, Sulfophobococcus, Thermodiscus, Thermosphaera* and *Thermoplasma.* Specific examples of archea include *A. aceticus, A. camini, A. fulgidus, A. infectus, A. lithotrophicus, A. pernix, A. profundus, A. veneficus, A. saccharovorans, A. sulfurreducens, C. dracosis, C. lagunensis, C. noboribetus, C. symbiosum, D. amylolyticus, D. fermentans, D. mobilis, D. mucosus, G. barossii, G. indica, G. pacifica, H. butylicus, N. maritimus, G. ahangari, H. paucihalophilus, H. mukohataei, H. katesii, H. zhouii, I. aggregans, I. islandicus, I. pacificus, I. hospitalis, M. aarhusense, M. alcaliphilum, M. beijingense, M. bryantii, M. congolense, M. curvum, M. espanolae, M. formicicum, M. ivanovii, M. oryzae, M. palustre, M. subterraneum, M. thermaggregans, M. uliginosum, N. amylolyticus, N. jeotgali, N. occultus, P. abyssi, P. brockii, P. occultum, P. fumarii, P. oshimae, P. torridus, S. hellenicus, S. marinus, S. hydrogenophila, S. zilligii, T. maritimus, T. aggregans, T. acidophilum, T.* sp. P61, *T.* sp. S01, *T.* sp. S02, *T.* sp. XT101, *T.* sp. XT102, *T.* sp. XT103, *T.* sp. XT107, and *T. volcanium.*

In some cases, an analyte may be any molecule derived from a mammal. In some cases, the mammal is a human, a non-human primate, mouse, rat, rabbit, goat, dog, cat, or cow. In some embodiments, the mammal is a human. In some cases, a human is a patient.

In some cases, an analyte may be any molecule derived from a plant. In some cases, a plant is any of various photosynthetic, eukaryotic, multicellular organisms of the kingdom Plantae characteristically producing embryos, containing chloroplasts, having cellulose cell walls, and lacking the power of locomotion.

In some cases, the methods provided in this disclosure may be used to detect any one of the analytes described above, or elsewhere in the specification. In some cases the methods provided in this disclosure may be used to detect panels of the analytes described above, or elsewhere in the specification. For example, a panel may comprise an analyte selected from the group consisting of any 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 500, 1000, 5000, 10,000, 100,000, or more analytes described above or elsewhere in the specification.

An analyte may be obtained from any suitable location, including from organisms, whole cells, cell preparations and cell-free compositions from any organism, tissue, cell, or environment. Analytes may be obtained from environmental samples, forensic samples, biopsies, aspirates, formalin fixed embedded tissues, air, agricultural samples, soil samples, petroleum samples, water samples, or dust samples. In some instances, an analyte may be obtained from bodily fluids which may include blood, urine, feces, serum, lymph, saliva, mucosal secretions, perspiration, central nervous system fluid, vaginal fluid, or semen. Analytes may also be obtained from manufactured products, such as cosmetics, foods, personal care products, and the like. Analytes may be the products of experimental manipulation including, recombinant cloning, polynucleotide amplification or polymerization, polymerase chain reaction (PCR) amplification or polymerization, isothermal amplification or polymerization, purification methods (such as purification of genomic DNA or RNA), and synthesis reactions.

More than one type of analyte may be detected in each multiplexed assay. For example, a polynucleotide, a protein, a polypeptide, a lipid, a carbohydrate, a sugar, a small molecule, or any other suitable molecule may be detected simultaneously in the same multiplexed assay with the use of suitable reagents. Any combination of analytes may be detected at the same time.

Detection of an analyte may be useful for any suitable application, including research, clinical, diagnostic, prognostic, forensic, and monitoring applications. Exemplary applications include detection of hereditary diseases, identification of genetic fingerprints, diagnosis of infectious diseases, cloning of genes, paternity testing, criminal identification, phylogeny, anti-bioterrorism, environmental surveillance, and DNA computing. For example, an analyte may be indicative of a disease or condition. An analyte may be used to make a treatment decision, or to assess the state of a disease. The presence of an analyte may indicate an infection with a particular pathogen, or any other disease, such as cancer, autoimmune disease, cardiorespiratory disease, liver disease, digestive disease, and so on. The methods provided herein may thus be used to make a diagnosis and to make a clinical decision based on that diagnosis. For example, a result that indicates the presence of a bacterial polynucleotide in a sample taken from a subject may lead to the treatment of the subject with an antibiotic.

In some cases, the methods and compositions of the present disclosure may be used to detect at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000, 100,000, or more analytes. In some cases the methods and compositions of the present disclosure may be used to detect about 1-10,000, 1-1000, 1-100, 1-50, 1-40, 1-30, 1-20, 1-10, or 1-5 analytes.

In some cases, this disclosure provides assays that are capable of unambiguously detecting the presence or absence of each of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000, or 100,000 analytes, in any combination of presence or absence, in a single sample volume. In some cases, this disclosure provides assays that are capable of unambiguously detecting the presence or absence of each of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000, or 100,000 analytes, in any combination of presence or absence, in a single sample volume. In some cases, this disclosure provides assays that are capable of unambiguously detecting the presence or absence of less than 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 250, 300, 350, 400, 450, 500, 600, 700, 800, 900, 1000, 2000, 3000, 4000, 5000, 6000, 7000, 8000, 9000, 10,000, or 100,000 analytes, in any combination of presence or absence, in a single sample volume.

A. Distance

In one aspect, the methods provided herein may be used to detect polynucleotide analytes containing about 1-1000 base pairs (bp). In some cases, the methods provided herein may be used to detect polynucleotide analytes containing 1-500 bp, 10-450 bp, 15-400 bp, 20-350 bp, 25-300 bp, 30-250 bp, 35-200 bp, or 40-190 bp. In some cases, the methods may be used to detect a polynucleotide analyte containing 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, or more base pairs. In some cases, the methods may be used to detect polynucleotide analyte containing at least 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, or 190 base pairs. In some cases, the methods may be used to detect polynucleotide analyte containing no more than 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, or 190 base pairs.

B. Sensitivity

In some cases, the methods disclosed herein may be used to detect polynucleotide analyte at concentrations of about 100 uM to about 1 fM. In some cases, the methods provided herein may be used to detect a polynucleotide analyte at concentrations of about 10 uM-20 fM, 1 uM-40 fM, 500 nM-60 fM, 100 nM-70 fM, 50 nM-80 fM, 30 nM-90 fM, 10 nM-100 fM. In some cases, the methods may be used to detect a polynucleotide analyte at a concentration of 10 nM, 9 nM, 8 nM, 7 nM, 6 nM, 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 180 pM, 160 pM, 140 pM, 120 pM, 100 pM, 95 pM, 90 pM, 85 pM, 80 pM, 75 pM, 70 pM, 65 pM, 60 pM, 55 pM, 50 pM, 45 pM, 40 pM, 35 pM, 30 pM, 25 pM, 20 pM, 18 pM, 16 pM, 14 pM, 12 pM, 10 pM, 8 pM, 6 pM, 4 pM, 2 pM, 1 pM, 900 fM, 800 fM, 700 fM, 600 fM, 500 fM, 400 fM, 300 fM, 200 fM, 100 fM, 50 fM, 10 fM, 1 fM, 100 aM, 10 aM, or 1 aM. In some cases, the methods may be used to detect a polynucleotide analyte at a concentration of at least 10 nM, 9 nM, 8 nM, 7 nM, 6 nM, 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 180 pM, 160 pM, 140 pM, 120 pM, 100 pM, 95 pM, 90 pM, 85 pM, 80 pM, 75 pM, 70 pM, 65 pM, 60 pM, 55 pM, 50 pM, 45 pM, 40 pM, 35 pM, 30 pM, 25 pM, 20 pM, 18 pM, 16 pM, 14 pM, 12 pM, 10 pM, 8 pM, 6 pM, 4 pM, 2 pM, 1 pM, 900 fM, 800 fM, 700 fM, 600 fM, 500 fM, 400 fM, 300 fM, 200 fM, 100 fM, 50 fM, 10 fM, 1 fM, 100 aM, 10 aM, or 1 aM. In some cases, the methods may be used to detect a polynucleotide analyte at a concentration of no more than 10 nM, 9 nM, 8 nM, 7 nM, 6 nM, 5 nM, 4 nM, 3 nM, 2 nM, 1 nM, 950 pM, 900 pM, 850 pM, 800 pM, 750 pM, 700 pM, 650 pM, 600 pM, 550 pM, 500 pM, 450 pM, 400 pM, 350 pM, 300 pM, 250 pM, 200 pM, 180 pM, 160 pM, 140 pM, 120 pM, 100 pM, 95 pM, 90 pM, 85 pM, 80 pM, 75 pM, 70 pM, 65 pM, 60 pM, 55 pM, 50 pM, 45 pM, 40 pM, 35 pM, 30 pM, 25 pM, 20 pM, 18 pM, 16 pM, 14 pM, 12 pM, 10 pM, 8 pM, 6 pM, 4 pM, 2 pM, 1 pM, 900 fM, 800 fM, 700 fM, 600 fM, 500 fM, 400 fM, 300 fM, 200 fM, 100 fM, 50 fM, 10 fM, 1 fM, 100 aM, 10 aM, or 1 aM.

C. Specificity

In some methods provided herein, a primer pair may be specific for one or a plurality of analytes. In some cases, a primer pair is specific to 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, a primer pair is specific to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, a primer pair is specific to less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 analytes. In some cases, a primer pair is specific to one analyte. In some cases, a primer pair is universal to all analytes.

V. Probes and Primers

Some of the methods provided in this disclosure utilize a reagent (e.g. an oligonucleotide such as a primer or a probe that is attached to a chromophore) that can generate a signal in the presence of an analyte. Any suitable reagent may be used with the present disclosure. Generally, a reagent will have an analyte-specific component and a component that generates a signal in the presence of the analyte. In some cases, these reagents are referred to as probes and primers. In some cases, the probes are hybridization probes. In some cases, the hybridization probes are oligonucleotide probes attached to chromophores. In some cases, the probes are antibodies that detect an analyte, with a fluorescent label that emits or is quenched upon binding of the antibody to an analyte. In some cases, the reagent is a primer. In some cases, the primer is attached to a chromophore. In some cases, the primer is attached to a fluorophore. In some cases, the primer is attached to a quencher.

The methods of the present disclosure may use one or more reagents (e.g., an oligonucleotide such as a primer or a probe that is attached to a chromophore) to detect the presence or absence of each analyte. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more reagents may be used to detect the presence or absence of each analyte. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 reagents may be used to detect the presence or absence of each analyte. In some cases, fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 reagents may be used to detect the presence or absence of each analyte.

In some cases, a sample is contacted with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more reagents to detect the presence or absence of all analytes. In some cases, a sample is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more reagents to detect the presence or absence of all analytes. In some cases, a sample is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 reagents to detect the presence or absence of all analytes.

As described above, primers attached to a fluorophore or a quencher may be used to detect the presence of an analyte in a polynucleotide amplification or polymerization assay. The quencher can quench the fluorescence emitted by the fluorophore upon excitation by a light source when the quencher and fluorophore are in close proximity. The sequence of the primer can be designed to be complementary to or may contain nucleotide mutations to a polynucleotide sequence present in an analyte, and the primer is capable of hybridizing to the analyte. The sequence of the primer can also be designed to contain one or more nucleotide variations in a polynucleotide sequence of an analyte, and the primer is capable of hybridizing to the analyte. A fluorophore can be attached to the 5' end of one of a primer pair. A quencher can be attached to the 5' end of the second primer of the primer pair. Hybridization of the primers may be performed in a nucleic acid amplification or polymerization reaction comprising primers (e.g., a polymerase chain reaction). Upon extension of the primers by a DNA polymerase, the fluorophore and quenchers are incorporated in the amplicon or amplification (or polymerization) product (e.g., an analyte). The incorporation of the quencher and the fluorophore in the newly generated amplicon can lead to signal generation (e.g., quenching of fluorescence intensity from the fluorophore). With each iterative amplification or polymerization reaction, the fluorescence intensity is reduced by a factor of about 2. The amount of fluorescence detected can be used to directly determine the amount of analyte present. If no analyte is present, little or no quenching will be observed.

In some cases, a sample to be analyzed is combined with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more pairs of primers (e.g. a forward primer and a reverse primer). In some cases a sample to be analyzed is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more pairs of primers. In some cases a sample to be analyzed is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 pairs of primers. In some cases, the number of pairs of primers is 2-10, 3-15, 4-20, 3-10, 4-10, 5-10, 6-8, or 6-10. In some cases, a sample to be analyzed is contacted with 1 pair of primers.

In some cases, a sample may contain one or more analytes. In some cases, one primer pair may be used to detect the presence or absence of each analyte. In some cases, a sample is contacted with 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000, or more different pairs of primers with each primer pair detecting a single analyte. In some cases, a sample is contacted with at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000, or more different pairs of primers with each primer pair detecting a single analyte. In some cases, a sample is contacted with fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, 10,000, or more different pairs of primers with each primer pair detecting a single analyte. In some cases, the number of pairs of primers is 2-10, 3-15, 4-20, 3-10, 4-10, 5-10, 6-8, or 6-10.

In some cases, primers may be specific for a particular analyte and capable of amplifying a region complementary to a probe. In some cases, the number of primers used is equivalent to the number of probes. In other cases, the number of probes used may exceed the number of primer used. In some cases, the number of primers and probes is defined by a ratio. In some cases, the ratio of primer to probe is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of probe to primer is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000.

As disclosed elsewhere herein, primers may have one or a plurality of fluorophores or quenchers per primer. For example, in some cases a primer may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores. A primer may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores. A primer may comprise fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores.

A primer may comprise 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more quenchers. A primer may comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 quenchers. A primer may comprise fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 quenchers.

Attachment of fluorophores and quenchers to a probe or a primer may be performed in the same reaction or in serial reactions. A series of reactions may be performed to attach probes or primers to at least one fluorophore and the reaction products may be mixed to generate a mixture of probes or primers with different fluorophores.

Although many aspects of the present disclosure are exemplified using nucleic acid-based probes and primers, one of ordinary skill in the art will readily recognize that other forms of probes and primers would work equally well with the examples described in this disclosure. For example, a binding molecule specific to an analyte could be used as a probe. Non-limiting exemplary binding molecules include an antibody recognizing an analyte, and generating a signal in the presence of an analyte.

The fluorescent labels of the present disclosure may be attached to a probe or primer at any location. In some cases, a single chromophore is attached to the primer at the 5' end. In some examples, multiple chromophores are attached to the primer with at least one chromophore attached at the 5' end. Methods of chromophore labeling are well defined in the art. See, e.g. Pesce et al, editors, Fluorescence Spectroscopy, Marcel Dekker, New York, (1971); White et al., Fluorescence Analysis: A Practical Approach, Marcel Dekker, New York. (1970); and the like. Further, there is extensive guidance in the literature for derivatizing reporter and quencher molecules for covalent attachment via common reactive groups that can be added to an oligonucleotide. See, e.g. U.S. Pat. No. 3,996,345; and U.S. Pat. No. 4,351,760. In examples that utilize chromophore labels as described herein, any suitable labeling techniques may be used.

VI. Chromophores

Chromophores are molecules capable of selective light absorption resulting in the coloration of these molecule containing compounds. The color arises when a molecule at an excited state releases energy in the form of light with a defined spectrum. Exemplary chromophores include, but are not limited to, a fluorochrome, a non-fluorochrome chromophore, a quencher (e.g. fluorescence quencher and a dark quencher), an absorption chromophore, a fluorophore, any organic or inorganic dye, metal chelate, or any fluorescent enzyme substrate. In some cases, the chromophore is a fluorochrome. In some cases, the fluorochrome is a fluorophore. In some cases, the chromophore is a quencher. In some cases, the chromophore is a dark quencher.

Several chromophores are described in the art, e.g. Berlman, Handbook of Fluorescence Spectra of Aromatic Molecules, 2nd Edition, Academic Press, New York, (1971). In examples that utilize fluorescent labels as described herein, any suitable fluorescent label may be used.

Exemplary fluorophores suitable for use with the present disclosure includes rhodamine, rhodol, fluorescein, thiofluorescein, aminofluorescein, carboxyfluorescein, chlorofluorescein, methylfluorescein, sulfofluorescein, aminorhodol, carboxyrhodol, chlororhodol, methylrhodol, sulforhodol; aminorhodamine, carboxyrhodamine, chlororhodamine, methylrhodamine, sulforhodamine, and thiorhodamine; cyanine, indocarbocyanine, oxacarbocyanine, thiacarbocyanine, merocyanine, cyanine 2, cyanine 3, cyanine 3.5, cyanine 5, cyanine 5.5, cyanine 7, oxadiazole derivatives, pyridyloxazole, nitrobenzoxadiazole, benzoxadiazole, pyren derivatives, cascade blue, oxazine derivatives, Nile red, Nile blue, cresyl violet, oxazine 170, acridine derivatives, proflavin, acridine orange, acridine yellow, arylmethine derivatives, auramine, crystal violet, malachite green, tetrapyrrole derivatives, porphin, phtalocyanine and bilirubin; 1-dimethylaminonaphthyl-5-sulfonate, 1-anilino-8-naphthalene sulfonate, 2-p-touidinyl-6-naphthalene sulfonate, 3-phenyl-7-isocyanatocoumarin, N-(p-(2-benzoxazolyl)phenyl) maleimide, stilbenes, pyrenes, 6-FAM (Fluorescein), 6-FAM (NHS Ester), Fluorescein dT, HEX, JOE (NHS Ester), MAX, TET, ROX, TAMRA, TARMA™ (NHS Ester), TEX 615, ATTO™ 488, ATTO™ 532, ATTO™ 550, ATTO™ 565, ATTO™ Rho101, ATTO™ 590, ATTO™ 633, ATTO™ 647N, TYE™ 563, TYE™ 665, TYE™ 705 and the like.

Exemplary quenchers suitable for use with the present disclosure includes black hole quenchers, such as BHQ-0, BHQ-1, BHQ-2, BHQ-3; ATTO quenchers, such as ATTO 540Q, ATTO580Q, and ATTO612Q; Qx1 quenchers; Iowa Black FG, Iowa Black RG, Iowa Black FQ and Iowa Black RQ; IRDye QC-1; 1.4 nm Nanogold; and the like.

The fluorophores that may be used with the disclosure are not limited to any of the fluorophores described herein. For example, fluorophores with improved properties are continually developed, and these fluorophores could readily be used with the methods provided in this disclosure. Such improved fluorophores include quantum dots, which may emit energy at different wavelengths after being excited at a single wavelength.

A. Chromophore Combinations

In some cases, a plurality of chromophores is attached to an oligonucleotide (e.g. a probe or a primer). In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more chromophores are attached to an oligonucleotide. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more chromophores are attached to an oligonucleotide. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 chromophores are attached to an oligonucleotide. In some cases, one chromophore is attached to an oligonucleotide.

In some cases, the oligonucleotide comprises a probe. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more chromophores are attached to a probe. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more chromophores are attached to a probe. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 chromophores are attached to a probe. In some cases, one chromophore is attached to a probe.

In some cases, the oligonucleotide is a primer. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more chromophores are attached to a primer. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more chromophores are attached to a primer. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 chromophores are attached to a primer. In some cases, one chromophore is attached to a primer. In some cases, one chromophore is attached at the 5' end of a primer. In some cases, a plurality of chromophores is attached to a primer with at least one chromophore attached at the 5' end of the primer.

In some cases, a plurality of fluorophores and quenchers is attached to a probe. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores are attached to a probe. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores are attached to a probe. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores are attached to a probe. In some cases, one fluorophore is attached to a probe. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more quenchers are attached to a probe. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more quenchers are attached to a probe. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 quenchers are attached to on a probe. In some cases, one quencher is attached to a probe.

In some cases, a combination of fluorophores and quenchers are attached to a probe. In some cases, the number of fluorophores and quenchers on a probe is defined by a ratio. In some cases, the ratio of fluorophore to quencher is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of fluorophore to quencher is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of quencher to fluorophore is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of quencher to fluorophore is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000.

In some cases, a plurality of fluorophores and quenchers is attached to a primer. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores are attached to a primer. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores are attached to a primer. In some cases, one fluorophore is attached to a primer. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores are attached to a primer. In some cases, one fluorophore is attached at the 5' end of a primer. In some cases, a plurality of fluorophores is attached to a primer with at least one fluorophore attached to the 5' end of the primer. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more quenchers are attached to a primer. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more quenchers are attached to a primer. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 quenchers are attached to a primer. In some cases, one quencher is attached to a primer. In some cases, one quencher is attached at the 5' end of a primer. In some cases, a plurality of quenchers is attached to a primer with at least one quencher attached at the 5' end of the primer.

In some cases, a combination of fluorophores and quenchers are attached to a primer. In some cases, the number of fluorophores and quenchers on a primer is defined by a ratio. In some cases, the ratio of fluorophore to quencher is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000. In some cases, the ratio of quencher to fluorophore is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90, 100, 200, 300, 400, 500, 600, 700, 800, 900, or 1000.

In some cases, multiple fluorophores are paired with one quencher. In some cases 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores are paired with one quencher. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores are paired with one quencher. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores are paired with one quencher. In some cases, multiple fluorophore and quencher pairs are used. In some cases, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophore and quencher pairs are used. In some cases, about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophore and quencher pairs are used. In some cases, less than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophore and quencher pairs are used. In some cases, 1 fluorophore and quencher pair is used.

In some cases, a pair of primers comprises a first primer and a second primer. In some cases, multiple fluorophores are attached to a first primer and one quencher is attached to a second primer. In some cases, at least one fluorophore is attached to the 5' end of the first primer. In some cases, the quencher is attached to the 5' end of the second primer. In some cases, multiple fluorophores are attached to a second primer and one quencher is attached to a first primer. In some cases, at least one fluorophore is attached to the 5' end of the second primer. In some cases, the quencher is attached to the 5' end of the first primer. In some cases, a fluorophore and a quencher are not attached to the same primer.

The skilled artisan will realize that the advantages of the present disclosed probes or primers may be retained while modifying various aspects of its structure. For example, but not by way of limitation, the number of donor/quencher pairs may be modified. The addition of more donor/quencher pairs to the probe or primer is expected to increase the amount of total fluorescence observable prior to initiation of amplification or polymerization reaction. There is no upper limit to the number of donor/quencher pairs that may be added to the probe or primer. In one example, the number of donor/quencher pairs is at least two, in other examples, the detector contains at least three or more donor/quencher pairs. In some examples, the detector may contain at least 10, 20, 30, or 50 pairs, or it may contain hundreds of donor/quencher pairs, as needed to produce, for example, an optimal signal-to-noise ratio and assay sensitivity.

In some cases, the methods provided in this disclosure may include the use of fluorophore/quencher pair as a control. The control fluorophore/quencher pair may be attached to one or more probe or primer pairs binding a positive control analyte, and each analyte to be detected, in a sample. If the same sequence occurs in the positive control analyte and each analyte to be detected, a single control primer pair may be used. If the same sequence does not occur in the positive control analyte and each analyte to be detected, different primer pairs may be used, but each primer pair may still be attached to the control fluorophore/quencher pair.

For example, building on the methods described above, one fluorophore/quencher pair may be used to encode the presence of a control analyte that is always present in the sample. The control analyte may be added to the sample, or may be inherently present in the sample. Additional fluorophore/quencher pairs may be used to encode the presence of additional analytes.

B. Signals

Disclosed herein is a method of utilizing the signal to identify the presence or absence of an analyte. In some cases, the signal is an increase in signal. In some cases, the signal is a decrease in signal. In some cases, a signature profile is generated based on the changes in signal at a specific distance. In some cases, once the length of an analyte is known, additional information can be extrapolated. In some cases, additional information includes the molecular weight of an analyte.

In some cases, a signal can be compared to a threshold value. A threshold can be defined as the average standard deviation of a baseline (or background) signal multiplied by an adjustable factor. In some cases, during a PCR experiment, reaction and environmental conditions related to each tube can influence fluorescence, and the fluorescence signal may fluctuate over time creating a background signal or baseline signal. This baseline signal can be determined, e.g., using the initial cycles of the PCR experiment used to detect an analyte. Alternatively, the background or baseline signal can be determined using a separate experiment. A standard deviation calculated from the mean of the baseline signal can then be used to establish a threshold. In some cases, the adjustable factor can be a factor of about 1, 1.1, 1.2, 1.3, 1.4, 1.5, 1.6, 1.7, 1.8, 1.9, 2, 3, 4, 5, 6, 7, 8, 9, 10, 20, 50, 100, or more. In some cases, the adjustable factor can be calculated prior to the start of an experiment. In some cases, the adjustable factor can vary with the type of chromophore used. In some cases, the adjustable factor can vary from experiment to experiment. In some cases, the adjustable factor can vary from instrument to instrument. In some cases, the adjustable factor is calculated for each instrument. In some cases, a threshold is established above the baseline signal. In some cases, a threshold is established below the baseline signal. In some cases, an observed signal (e.g. the signal that is measured to detect an analyte) crosses the threshold level. In some cases, an observed signal does not cross the threshold level. In some cases, the observed signal that crosses the threshold indicates a presence of the product analyte. In some cases, the observed signal that does not cross the threshold indicates an absence of the product analyte.

In some cases, a reference signal or reference signal range is established which can be used, for example, as a control for any of the methods described herein. In some cases, the reference signal or reference signal range can be used to determine whether an amplification or polymerization reaction described herein is performed successfully. For example, prior to initiating a PCR experiment involving the use of a chromophore, a reference signal range for the chromophore can be generated. The reference signal range can be generated by determining the values of two components, X and Y, such that the reference signal range is X±Y. In some cases, the X component is the mean fluorescence signal of the chromophore with respect to temperature and time, and the Y component is the standard deviation of X. When used as a control during a PCR reaction, a signal from each denaturation step can be compared with the reference signal or reference signal range. A signal outside of the reference signal range can indicate that the reaction has failed while a signal within the reference signal range can indicate that the reaction has succeeded. In some cases, the reference signal or reference signal range can be used as a cycle-by-cycle control. In some cases, the reference signal or reference signal range can be used as an internal control. In some cases, the method of calculating the reference signal or reference signal range is the same as calculating the baseline signal, e.g. establishing the mean of a fluorescence signal and calculating its standard deviation.

In some cases, the denaturation signal is used for normalization during an amplification or polymerization experiment. For example, when the denaturation signal is within the reference signal range, the denaturation signal can be used for normalization. During the course of each amplification or polymerization cycle, the denaturation signal can be used to normalize the signal measured during the annealing step, thereby generating an internal normalization for each cycle, e.g. similar to the chopper stabilization where the signal can be reset to a particular value or unit, for example, a value of 1. In some cases, the denaturation signal is used for internal or self normalization. In some cases, the methods described herein use the denaturation signal of each cycle for a cycle-by-cycle self-normalization.

In some cases, the annealing signal is used to determine the presence or absence of an analyte. In some cases, when the annealing signals are compared between consecutive steps using the cycle-by-cycle self-normalization method described previously, a relative change in signals can be determined. In some cases, the relative signal change can be referred to as a relative quantitation of signals. In some cases, the relative quantitation of signals is used to determine the presence or absence of an analyte. In some cases, the annealing signal is compared to a standard to determine the presence of an analyte. In some cases, the standard is referred to as a standard ladder or a control signature profile, described elsewhere herein in this disclosure. In some cases, the comparison of the annealing signal to a standard ladder is referred to as a relative quantification of the analyte. In some cases, the methods described herein use a relative quantification method to determine the presence or absence of an analyte.

In some cases, the methods presented in this disclosure may be used with any quantifiable signal. As described herein and elsewhere herein, a coding scheme may be utilized to indicate a multiplicity of signals based on color. In some cases, the coding scheme is equally applicable to any other method providing a quantifiable signal, including an electrochemical signal and a chemiluminescent signal.

In some cases, if a fluorescent signal is employed, the number of analytes that can be encoded may be further expanded by utilizing additional fluorophores. For example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or more fluorophores may be used. In some cases, at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores may be used. In some cases, fewer than 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 fluorophores may be used.

Signals can be measured and compared at various points during a detection method described herein. For example, during an amplification or polymerization reaction (e.g., a PCR reaction or process), pairwise signals can be measured. In some cases, a signal can be measured: before annealing, during or after annealing of the primers to the template (e.g., analyte); before, during or after denaturing the double stranded template; or before the annealing step or after the denaturing step. A signal signature as described herein can be generated using these measurements.

C. Signature Profiles

A signature profile typically comprises a plurality of signals. In some cases, a signal includes an electrochemical signal, a chemiluminescence signal and a fluorescence signal. In some cases, a signature profile contains a plurality of fluorescence signals. In some cases, a profile curve is generated from the plurality of florescence signals. In some cases, a signature profile contains an initial fluorescence signal and an end-point fluorescence signal. In some cases, a signature profile contains signals measured during the annealing step of an amplification or polymerization reaction. In some cases, a fluorescence signal is influenced by external factors. In some cases, the external factors include temperature, pH, organic and inorganic agents (e.g. salts, urea, DMSO) and addition or removal of chromophores.

In some cases, signature profiles are generated from different types of detection experiments. In some cases, a signature profile generated from a polynucleotide morphology study is referred to as a morphology curve. In some cases, a signature profile generated from a denaturation study is referred to as a melt curve. In some cases, a signature profile generated from a persistence length study is referred to as a length curve. In some cases, a signature profile generated from a single-nucleotide polymorphism (SNP) study is referred to as a SNP curve.

In some cases, the change in signal can be calculated as a percentage of change. In some cases, the percentage of signal change is 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 300, 400, 500, 600, 700, 800, 900, 1000, 10,000%. In some cases, the percentage of signal change is about 0.01, 0.1, 0.2, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 150, 200, 300, 400, 500, 600, 700, 800, 900, 1000, 10,000%.

VII. Analytical Techniques and Instrumentation

The methods described in this disclosure are compatible with a variety of amplification or polymerization methods, including polymerase chain reaction (PCR), ligase chain reaction (LCR), replicase-mediated amplification, strand-displacement amplification (SDA), "rolling circle" types of amplification, and various transcription associated amplification or polymerization methods. See, e.g., PCR amplification: U.S. Pat. Nos. 4,683,195, 4,683,202, and 4,800,159; LCR amplification: U.S. Pat. No. 5,516,663 and EP 0320308 B1; replicase-mediated amplification: U.S. Pat. No. 4,786,600; SDA amplification: U.S. Pat. Nos. 5,422,252 and 5,547,861; rolling circle types of amplification: U.S. Pat. Nos. 5,714,320 and 5,834,252; and transcription associated amplification: U.S. Pat. Nos. 5,399,491, 5,554,516, 5,130,238, 5,437,990, 4,868,105 and 5,124,246, PCT Pub. WO 1988/010315 A1, and US Pub. 2006-0046265 A1, which are hereby incorporated by reference.

In some cases, the polymerase chain reaction (PCR) is a multiplex-PCR, a variable number of tandem repeats (VNTR) PCR, an asymmetric PCR, long PCR, a nested PCR, a hot-start PCR, a Touchdown PCR, an assembly PCR, a colony PCR, a quantitative PCR (qPCR), an end point PCR, a reverse transcriptase PCR, a digital PCR, or a droplet digital PCR. In some cases, the PCR process is a quantitative PCR process.

In some cases, the PCR amplification or polymerization step of the present disclosure can be performed by standard techniques well known in the art (See, e.g., Sambrook, E. F. Fritsch, and T. Maniatis, Molecular Cloning: A Laboratory Manual, Second Edition, Cold Spring Harbor Laboratory Press (1989); U.S. Pat. No. 4,683,202; and PCR Protocols: A Guide to Methods and Applications, Innis et al., eds., Academic Press, Inc., San Diego (1990) which are hereby incorporated by reference). PCR cycling conditions typically consist of an initial denaturation step, which can be performed by heating the PCR reaction mixture to a temperature ranging from about 80° C. to about 105° C. for times ranging from about 1 to about 10 min. Heat denaturation is typically followed by a number of cycles, ranging from about 1 to about 80 cycles, each cycle usually comprising an initial denaturation step, followed by a primer annealing step and concluding with a primer extension step. Enzymatic extension of the primers by a nucleic acid polymerase; e.g. Taq polymerase, produces copies of the template (e.g., an analyte) that can be used as templates in subsequent cycles. In some cases, the denaturation temperature is about 85° C. to about 100° C. In some cases, the denaturation temperature is 85° C., 86° C., 87° C., 88° C., 89° C., 90° C. 91° C. 92° C., 93° C., 94° C., 95° C., 96° C., 97° C., 98° C., 99° C., or 100° C. In some cases; the denaturation temperature is at least 85° C., 86° C., 87° C., 88° C., 89° C., 90° C., 91° C., 92° C., 93° C., 94° C., 95° C., 96° C., 97° C., 98° C., 99° C., or 100° C. In some cases, the denaturation temperature is no more than 85° C., 86° C., 87° C., 88° C., 89° C., 90° C., 91° C., 92° C., 93° C., 94° C., 95° C., 96° C., 97° C., 98° C., 99° C., or 100° C. In some cases, the annealing temperature is about 25° C. to about 80° C. In some cases, the annealing temperature is 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. In some cases, the annealing temperature is at least 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. In some cases, the annealing temperature is no more than 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C. 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. In some cases, the extension temperature is 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66"C, 67° C., 68° C., 69° C., 70° C., 71° C., 72° C., 73° C., 74° C., 75° C., 76° C., 77° C., 78° C., 79° C., or 80° C. In some cases, the extension temperature is at least 25° C. 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. In some cases, the extension temperature is no more than 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 46° C., 47° C., 48° C., 49° C., 50° C., 51° C., 52° C., 53° C., 54° C., 55° C., 56° C. 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C., or 80° C. In some cases, the number of cycles ranges from about 1, 2, 3, 4, 5, 6, 7, 8, 9, 10, 15, 20, 25, 30, 35, 40, 45, 50, 55, 60, 65, 70, 75 to about 80 cycles.

The methods provided herein are suitable for use with a variety of detection methods. For example, the methods may be applied using an analytical technique that measures a fluorescent signal. For example, many real-time PCR, quantitative PCR and droplet digital PCR instruments comprising an excitation light source that enable the detection of fluorescent signals can be used. Therefore, the methods of the present disclosure can be readily applied using instruments widely used in the art.

VIII. Diseases

The methods described herein can be used, for example, to detect one or more analytes associated with a disease or one or more genetic variations (e.g., a SNP) associated with a disease. A disease is an abnormal condition of an organism. In some cases, the organism is a mammal, such as a human, non-human primate, mouse, rat, rabbit, goat, dog, cat, or cow. In some cases, the mammal is a human. In some cases, the human is a patient or subject. In some cases, the disease is a genetic disorder, an autoimmune disease, a neurological disease, a cardiovascular disease or a cancer.

A genetic disorder is a disease caused by one or more abnormalities in the genome. Exemplary genetic disorders include 22q11.2 deletion syndrome, Acrocephaly, Acute cerebral Gaucher's disease, Adrenal gland disorders, Adrenogenital syndrome, Alzheimer's disease, Amelogenesis imperfect, androgen insensitivity syndrome, anemia, Angelman syndrome, Apert syndrome, ataxia telangiectasia, Canavan disease, Charcot-Marie-Tooth disease, Color blindness, Cri du chat, Cystic fibrosis, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Tay-Sachs disease and Turner syndrome.

An autoimmune disease is a disease caused when the immune system mistakenly attacks and destroys healthy body tissue. Exemplary autoimmune diseases include lopecia areata, autoimmune hemolytic anemia, autoimmune hepatitis, dermatomyositis, diabetes (type 1), several forms of juvenile idiopathic arthritis, glomerulonephritis, Graves' disease, Guillain-Barré syndrome, idiopathic thrombocytopenic purpura, myasthenia gravis, several forms of myocarditis, multiple sclerosis, pemphigus/pemphigoid, pernicious anemia, polyarteritis nodosa, polymyositis, primary biliary cirrhosis, psoriasis, rheumatoid arthritis, scleroderma/systemic sclerosis, Sjögren's syndrome, systemic lupus erythematosus, several forms of thyroiditis, several forms of uveitis, vitiligo, and granulomatosis with polyangiitis (Wegener's).

Exemplary neurological diseases include attention deficit hyperactivity disorder (ADHD), ALS, Alzheimer's disease, bipolar disorder, Bell's palsy, birth defects of the brain and spinal cord, cerebral palsy, chronic fatigue syndrome, dyslexia, epilepsy, Guillain-Barré syndrome, multiple sclerosis, muscular dystrophy, neuropathy, neuromuscular and related diseases, Parkinson's disease, schizophrenia, scoliosis and spinal deformity.

Exemplary cardiovascular disease include acute myocardial infarction, angina, arrhythmia, atherosclerosis, cardiomegaly, cardiomyopathy, carotid artery disease, congenital heart disease, congestive heart failure, coronary artery disease, endocarditis, fluid around the heart, hypertension, infective endocarditis, mitral valve prolapsed, peripheral artery disease, stroke, and valvular heart disease.

Cancer is characterized by an abnormal growth of cells. Exemplary cancer include bladder, brain, breast, bone, cervical, colon, esophageal, kidney, liver, lung, ovarian, pancreatic, proximal or distal bile duct, prostate, skin, stomach, thyroid, and uterine cancer.

Figure 3:
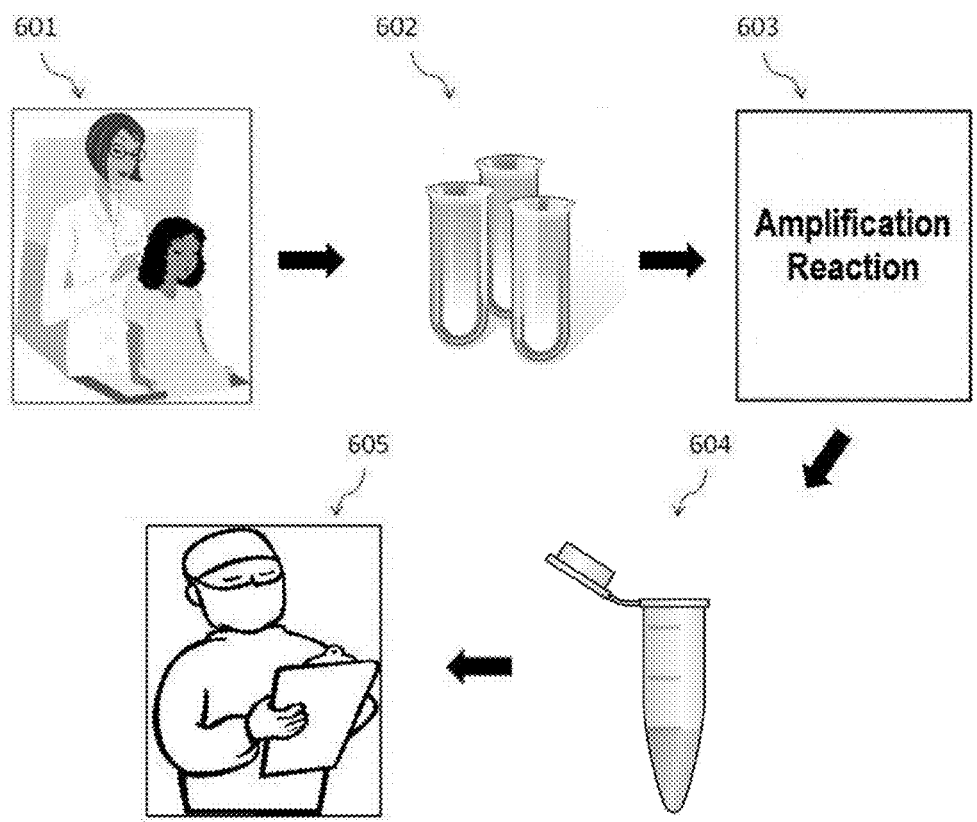
FIG. 3 illustrates a diagnostic protocol and treatment method for use with a detection method described herein.

In some cases, the presence of an analyte or a genetic variation in an analyte (e.g., a SNP) can serve as a disease marker. In some cases, the method disclosed herein can be used to detect a disease marker. In some cases, the method disclosed herein can be applicable in determining the presence or absence or the type of diseases affecting a patient. For example, FIG. 3 illustrates an overview of a method of providing a treatment in conjunction with a detection method described herein. 601 illustrates a clinician preparing to take a sample from a patient. In some cases, the sample can be a blood sample. In some cases, the sample can be a tissue sample. 602 illustrates a sample diluted into three concentrations (e.g. a separate concentration in each tube). 603 indicates an amplification or polymerization step (e.g., PCR). 604 illustrates products of the amplification or polymerization step. 605 depicts a clinician returning the results of an analysis to a patient.

IX. Compositions and Kits

This disclosure also provides compositions and kits for use with the methods described herein. The compositions may comprise any component, reaction mixture and/or intermediate described herein, as well as any combination thereof. For example, the disclosure provides detection reagents for use with the methods provided herein. Any suitable detection reagents may be provided, including a primer pair attached to two different chromophores (e.g., a fluorophore and a quencher), as described elsewhere in the specification.

In some cases, compositions comprise a first and a second primer or probe for the detection of at least one analyte wherein the primers are attached to either a fluorophore or a quencher at the 5' end. In some cases, compositions comprise primers attached at the 5' end with either a fluorophore or a quencher for the detection of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 10000 analytes. In some cases, compositions comprise primers attached to multiple different fluorophores or quenchers wherein at least one fluorophore or quencher is at the 5' end for the detection of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 10000 analytes. In some cases the compositions comprise multiple pairs of first and second primers, wherein each pair of first and second primers comprise either a fluorophore or a quencher at the 5' end. In some cases each pair of first and second primers comprise a different fluorophore and quencher from the remaining set of primers. In some cases the compositions comprise at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1000, 5000, or 10000 pairs of first and second primers.

The present disclosure also provides kits for carrying out the methods of the invention. Accordingly, a variety of kits are provided in suitable packaging. The kits may be used for any one or more of the uses described herein, and, accordingly, may contain instructions for detecting the presence or absence of each analyte or a plurality of analytes. A kit may be a diagnostic kit, for example, a diagnostic kit suitable for the detection of one or more analytes, including the analytes recited herein. A kit may contain any of the compositions provided in this disclosure, including those recited above.

X. Services

The methods provided herein may also be performed as a service. For example, a service provider may obtain the identity of a plurality of analytes that a customer wishes to analyze. The service provider may then encode each analyte to be detected by any of the methods described herein and provide appropriate reagents to the customer for the assay. The customer may perform the assay and provide the results to the service provider for decoding. The service provider may then provide the decoded results to the customer. The customer may also encode analytes, generate probes, and/or decode results by interacting with software installed locally (at the customer's location) or remotely (e.g., on a server reachable through a network). Exemplary customers include clinical laboratories, physicians, manufacturers of food and consumer products, industrial manufacturers (e.g., petroleum companies) and the like. A customer or party may be any suitable customer or party with a need or desire to use the methods, systems, compositions, and kits of the invention.

A. Server

Figure 4:
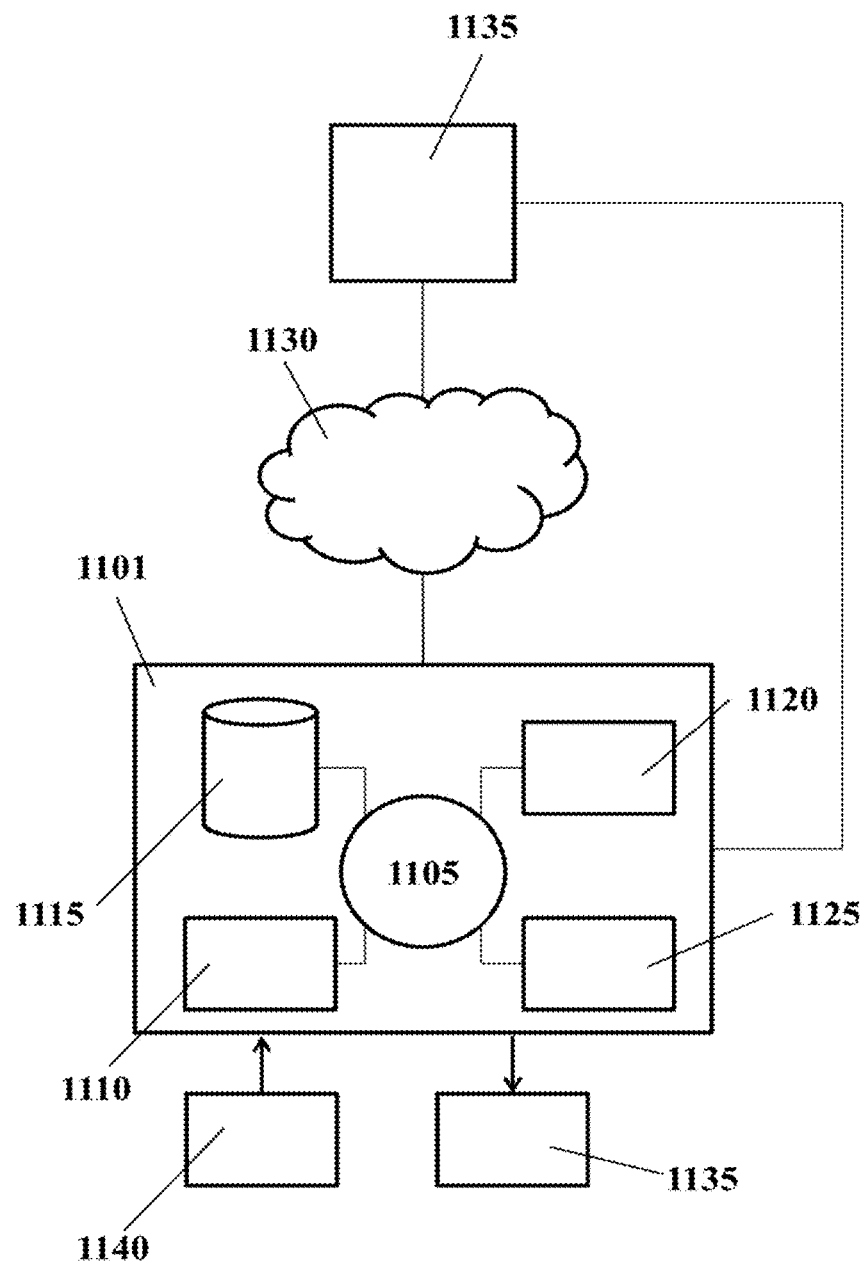
FIG. 4 illustrates a conceptual schematic of an exemplary computer server to be used for processing a method described herein.
Figure 5A:
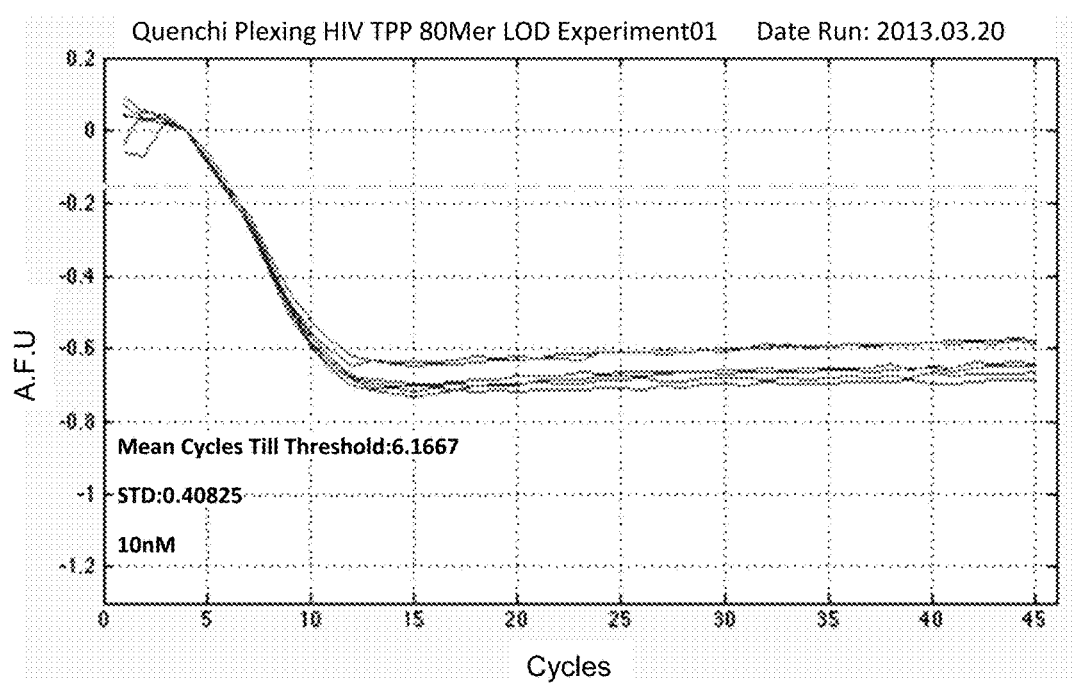
FIG. 5A-FIG. 5D exemplify the detection of HIV TPP analytes at varying concentrations using quantitative PCR (qPCR).
Figure 5B:
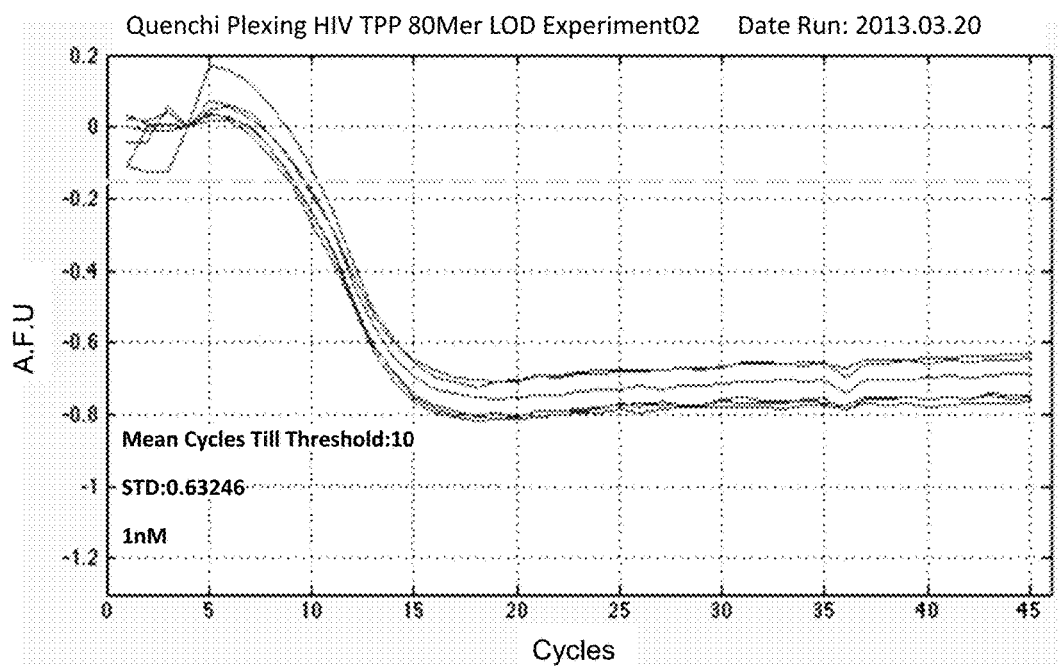
Figure 5C:
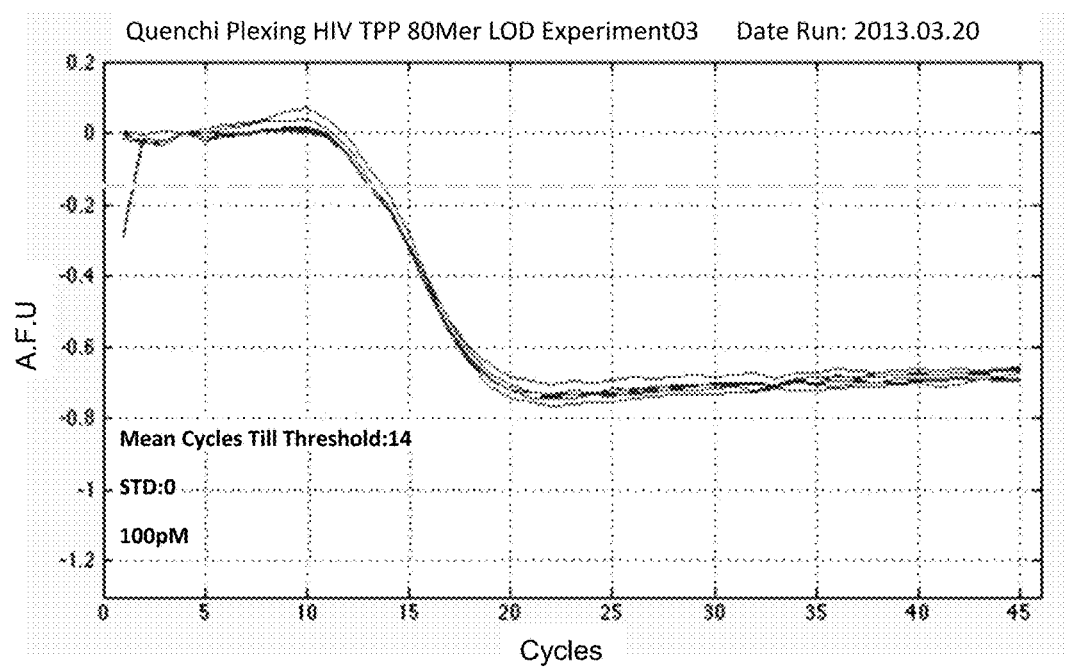
Figure 5D:
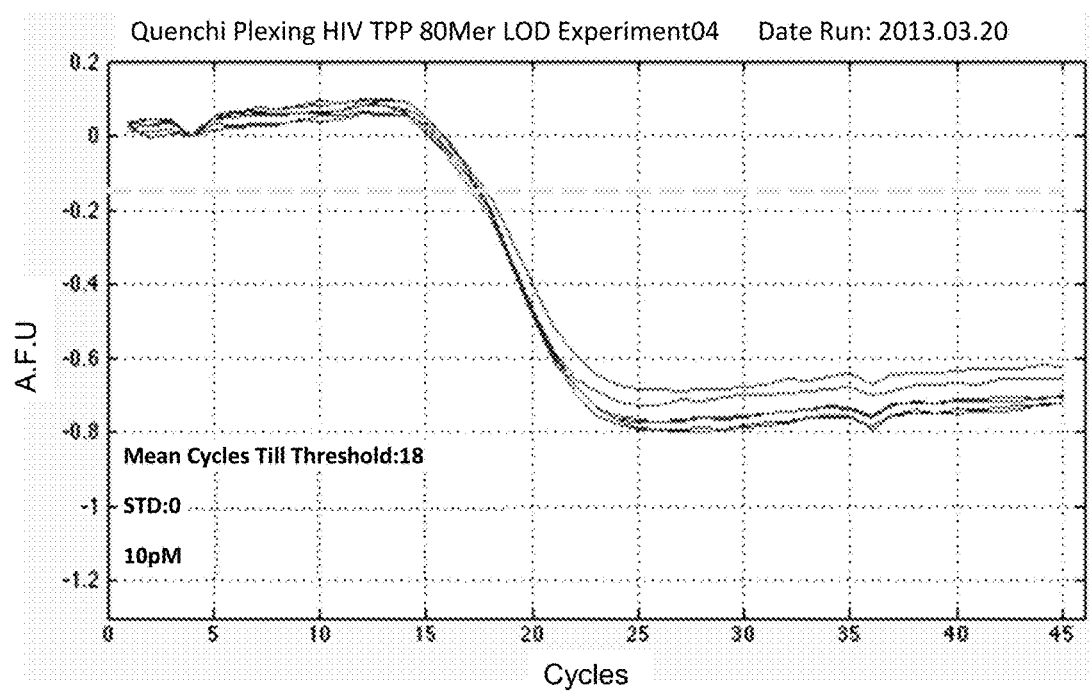
Figure 6A:
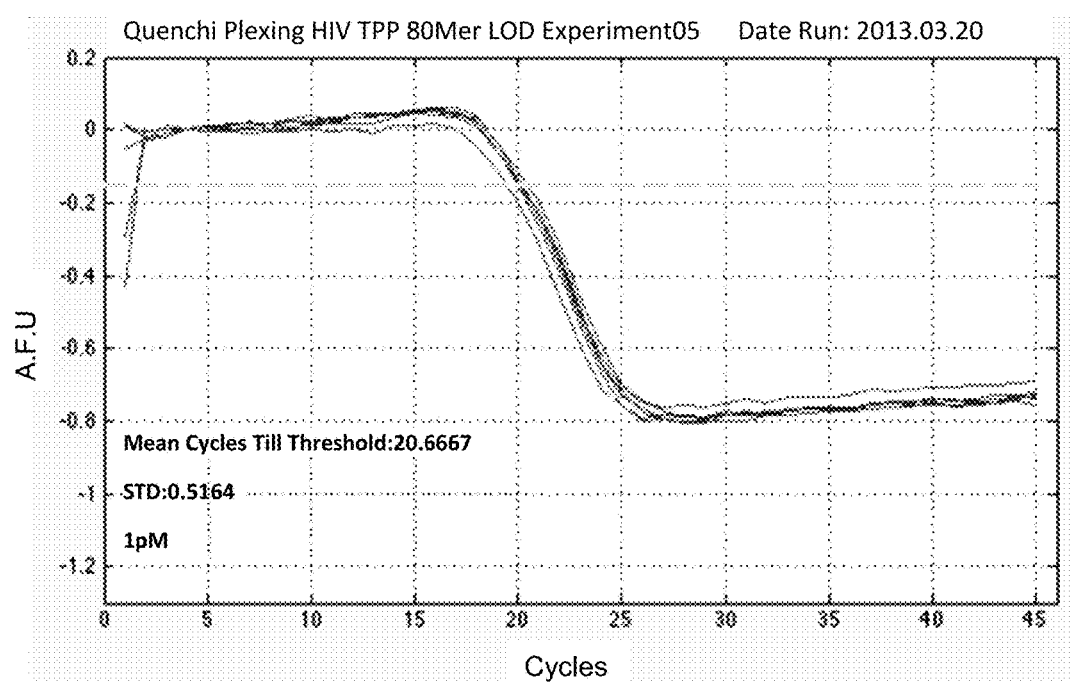
FIG. 6A-FIG. 6D illustrate the sensitivity of detection of HIV TPP using an exemplary detection method.
Figure 6B:
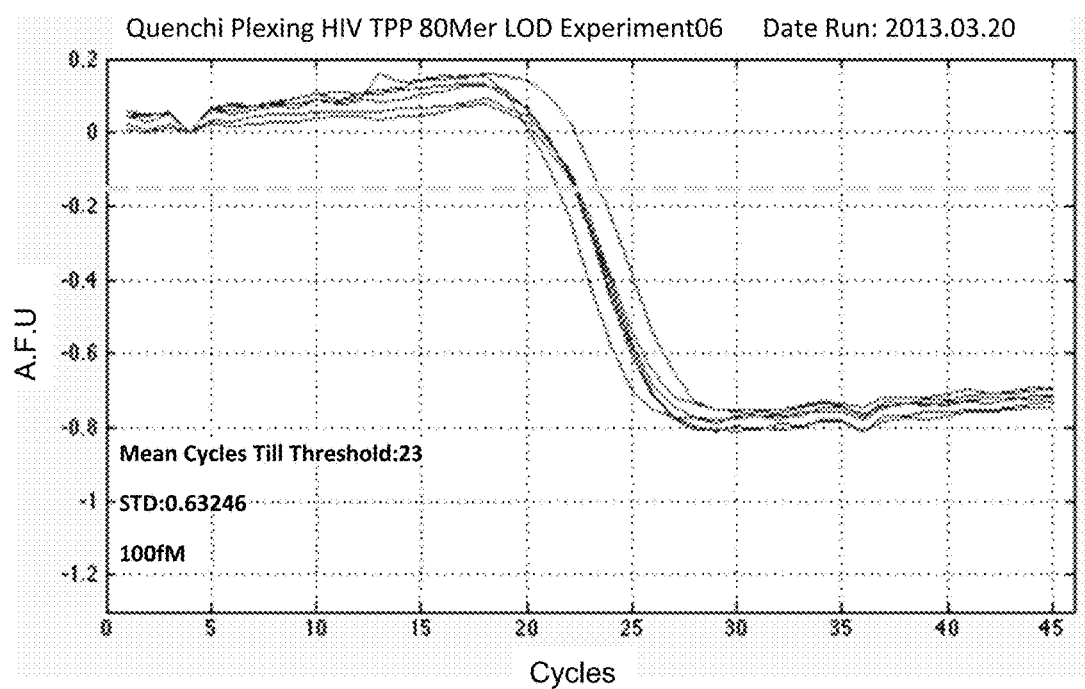
Figure 6C:
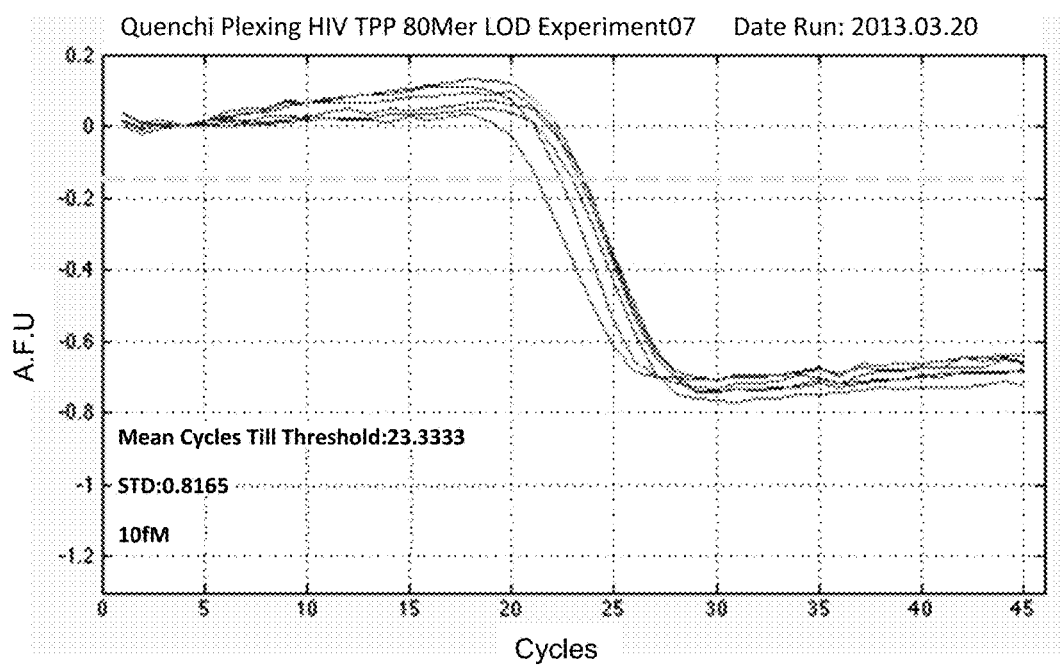
Figure 6D:
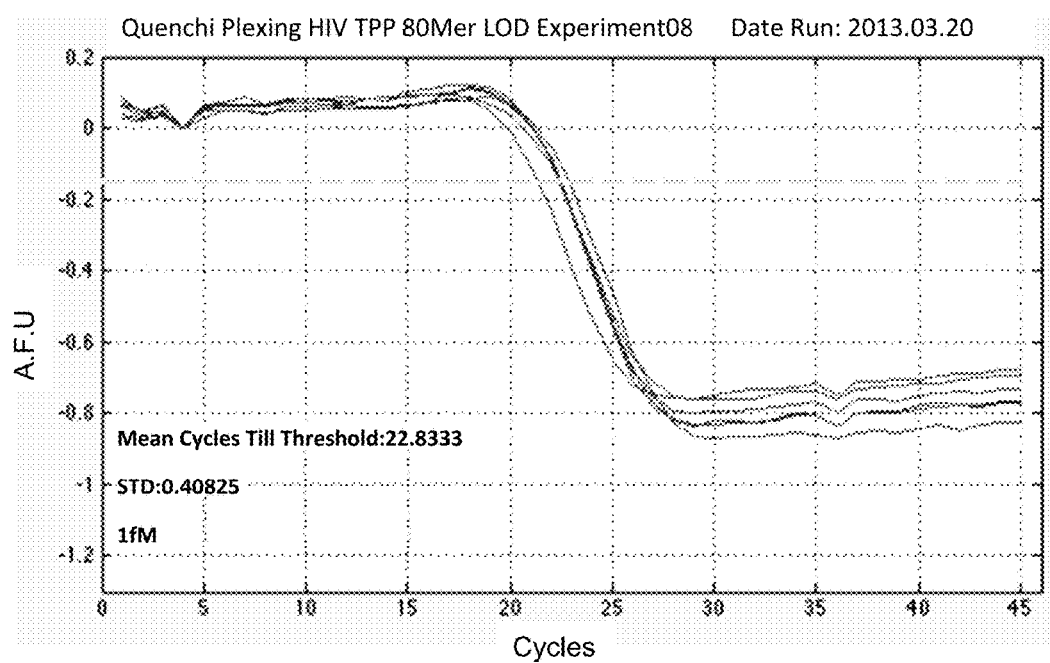

The methods provided herein may be processed on a server or a computer server (FIG. 4). The server 1101 includes a central processing unit (CPU, also "processor") 1105 which can be a single core processor, a multi core processor, or plurality of processors for parallel processing. A processor used as part of a control assembly may be a microprocessor. The server 1101 also includes memory 1110 (e.g. random access memory, read-only memory, flash memory); electronic storage unit 1115 (e.g. hard disk); communications interface 1120 (e.g. network adaptor) for communicating with one or more other systems; and peripheral devices 1125 which may include cache, other memory, data storage, and/or electronic display adaptors. The memory 1110, storage unit 1115, interface 1120, and peripheral devices 1125 are in communication with the processor 1105 through a communications bus (solid lines), such as a motherboard. The storage unit 1115 can be a data storage unit for storing data. The server 1101 is operatively coupled to a computer network ("network") 1130 with the aid of the communications interface 1120. A processor with the aid of additional hardware may also be operatively coupled to a network. The network 1130 can be the Internet, an intranet and/or an extranet, an intranet and/or extranet that is in communication with the Internet, a telecommunication or data network. The network 1130 in some cases, with the aid of the server 1101, can implement a peer-to-peer network, which may enable devices coupled to the server 1101 to behave as a client or a server. In general, the server may be capable of transmitting and receiving computer-readable instructions (e.g., device/system operation protocols or parameters) or data (e.g., sensor measurements, raw data obtained from detecting nucleic acids, analysis of raw data obtained from detecting nucleic acids, interpretation of raw data obtained from detecting nucleic acids, etc.) via electronic signals transported through the network 1130. Moreover, a network may be used, for example, to transmit or receive data across an international border.

The server 1101 may be in communication with one or more output devices 1135 such as a display or printer, and/or with one or more input devices 1140 such as, for example, a keyboard, mouse, or joystick. The display may be a touch screen display, in which case it may function as both a display device and an input device. Different and/or additional input devices may be present such an enunciator, a speaker, or a microphone. The server may use any one of a variety of operating systems, such as for example, any one of several versions of Windows, or of MacOS, or of Unix, or of Linux.

The storage unit 1115 can store files or data associated with the operation of a device or method described herein.

The server can communicate with one or more remote computer systems through the network 1130. The one or more remote computer systems may be, for example, personal computers, laptops, tablets, telephones, Smart phones, or personal digital assistants.

In some situations a control assembly includes a single server 1101. In other situations, the system includes multiple servers in communication with one another through an intranet, extranet and/or the Internet.

The server 1101 can be adapted to store device operation parameters, protocols, methods described herein, and other information of potential relevance. Such information can be stored on the storage unit 1115 or the server 1101 and such data can be transmitted through a network.

EXAMPLES

Example 1: DNA Sequences, Primers and Probes

Synthetic nucleic acid analytes from the Human Immunodeficiency Virus 1 (HIV-1) poly protease gene were chosen for exemplary detection studies using an amplification or polymerization technique. Templates from this gene, of lengths varying from 40 bp-80 bp, were synthesized.

Seven nucleic acid analytes from organisms of clinical relevance were chosen for exemplary detection studies using a multiplex PCR technique. These analytes include Influenza type A (InfA), influenza type B (InfB), respiratory syncytial virus type A (RsvA), respiratory syncytial virus type B (RsvB), human rhinovirus (Hrv), and human metapneumovirus (Hmpv). An additional analyte for human parainfluenza virus type 3 (PIV-3) was included to run as an orthogonal control. Multiplex analytes were coded using a binary scheme described elsewhere herein in this disclosure.

All oligonucleotides were synthesized by Integrated DNA Technologies (Coralville, Iowa). Diagnostic sequences were input into IDT's OligoAnalyzer 3.1 tool. Probes and primer pairs for each analyte were chosen, from the OligoAnalyzer's set of generated sequences, to minimize homology with un-intended analytes, probes and primers. Forward primers for all analytes were synthesized with a fluorophore at the 5' end, while the reverse primes for all analytes were synthesized with a quencher at the 5' end. Sequence information is tabulated in Tables 1 to 8. Nucleic acid products were synthesized and lyophilized by IDT. All nucleic acid analytes were reconstituted in TE buffer, ph7 (Life Technologies, Carlsbad, Calif.). Dilutions were done using UltraPure RNAse-free Water (Life Technologies, Carlsbad, Calif.).

Example 2: Primer Design

Specific primers and probes were designed using conserved regions of the analyte genes. Primers for Influenza A and B were designed in the nucleoprotein genes; Primers for RSV A and RSV B were designed in the conserved Fusion protein gene; Primers for HRV were designed in the 5'-UTR region; Primers for HMPV were designed in the Fusion protein gene; Primers for human PIV-3 were designed in conserved regions of the haemagglutinin genes.

Established GenBank Accession nos. were used for Influenza A, Influenza B, HRV, HMPV, and PIV-3. For RSV A and RSV B, primers used in previous studies (Jansen et al. "Development and evaluation of a four-tube real time multiplex PCR assay covering fourteen respiratory viruses, and comparison to its corresponding single target counterparts." *Journal of Clinical Virology* 51.3 (2011): 179-185; and Chun et al. "Dual priming oligonucleotide system for the multiplex detection of respiratory viruses and SNP genotyping of CYP2C19 gene." *Nucleic Acids Research* 35.6 (2007): e40) were inputted into BLAST and Accession nos. corresponding to high homology with complete coding sequence information were chosen. Accession nos. for virus sequences used in primer design can be found in Tables 2-8. Sequences were uploaded into Primer Quest software (Integrated DNA Technologies, Coralville, Iowa) with parameters set to take into account primer size, amplicon size, G-C %, similarity of reaction kinetics. A BLAST search was performed to check the specificity of the sequences of the primers and probes. Chosen primer pairs were entered into OligoAnalyzer 3.1 and analyzed for self-dimerization and hetero-dimerization. Primer sequences and their properties can be found in Tables 2-8. Sequence identifier numbers can be found in Tables 1-8.

TABLE 1

HIV-1 Poly Protease Sequence Information

| SEQ ID NO. | Sequence Information | HIV-1 40mer, 60mer, and 80mer |
|---|---|---|
|  | Source | HIV-1 Reference Sequence, Los Alamos National Laboratory |
| SEQ ID NO: 1 | 40Mer Template | 5'- GGA AGC TCT ATT AGA TAC AGA CAC CTG TCA ACA TAA TTG G -3' |
| SEQ ID NO: 2 | 60Mer Template | 5'- GGA AGC TCT ATT AGA TAC AGA TGA TAC AGT ATT AGA AGA AAC ACC TGT CAA CAT AAT TGG -3' |
| SEQ ID NO: 3 | 80Mer Template | 5'- GGA AGC TCT ATT AGA TAC AGA TGA TAC AGT ATT AGA AGA AAT GAG TTT GCC AGG AAG ATG ACA CCT GTC AAC ATA ATT GG -3' |
| SEQ ID NO: 4 | FWD Primer | 5'-/5Cy3/GG AAG CTC TAT TAG ATA CAG -3' |
| SEQ ID NO: 5 | RWD Primer | 5'-/5IABkFQ/CC AAT TAT GTT GAC AGG TGT -3' |

TABLE 2

Influenza type A sequence information

| SEQ ID NO. | Sequence Information | Influenza A |
|---|---|---|
|  | Source | GenBank Accession #M23976.1 Influenza A |
| SEQ ID NO: 6 | 85Mer Template | 5'- GTA GGG ATA GAG CCT TTC AAA CTG CTT CAA AAC AGC CAA GTA TAC AGC CTA ATC AGA CCG AAT GAG AAT CCA GCA CAC AAG AGT C -3' |
| SEQ ID NO: 7 | FWD Primer | 5'- GTA GGG ATA GAC CCT TTC AAA CTG -3' |
| SEQ ID NO: 8 | RWD Primer | 5'- GAC TCT TGT GTG CTG GAT TCT C -3' |
| SEQ ID NO: 9 | TaqMan Probe | 5'-/56-FAM/AG CCA AGT ATA CAG CCT AAT CAG ACC GA/3BHQ_1/-3' |
| SEQ ID NO: 10 | FWD qPrimer | 5'-/5Cy3/GT AGG GAT AGA CCC TTT CAA ACT G -3' |
| SEQ ID NO: 11 | RWD qPrimer | 5'-/5IABkFQ/GA CTC TTG TGT GCT GGA TTC TC -3' |
| SEQ ID NO: 12 | FWD Mistake qPrimer | 5'-/5Cy3/GT AGG GAG AGA CCC TTT CAA ACT G -3' |

TABLE 3

Influenza type B sequence information

| SEQ ID NO. | Sequence Information | Influenza B |
|---|---|---|
|  | Source | GenBank Accession # AB036876 Influenza B |
| SEQ ID NO: 13 | 81Mer Template | 5'- GTG CTT CCC ATA AGC ATT TAC GCC AAA ATA CCT CAA CTA GGG TTC AAC GTT GAA GAG TAC TCT ATG GTT GGG TAT GAA GCC -3' |
| SEQ ID NO: 14 | FWD Primer | 5'- GTG CTT CCC ATA AGC ATT TAC G -3' |
| SEQ ID NO: 15 | RWD Primer | 5'- GGC TTC ATA CCC AAC CAT AGA G -3' |
| SEQ ID NO: 16 | TaqMan Probe | 5'-/56-FAM/CC TCA ACT AGG GTT CAA CGT TGA AGA GT/3BHQ_1/-3' |
| SEQ ID NO: 17 | FWD qPrimer | 5'-/5Cy3/GT GCT TCC CAT AAG CAT TTA CG -3' |
| SEQ ID NO: 18 | RWD qPrimer | 5'-/5IABkFQ/GG CTT CAT ACC CAA CCA TAG AG -3' |

TABLE 4

Respiratory syncytial virus type A sequence information

| SEQ ID NO. | Sequence Information | Respiratory syncytial virus type A |
|---|---|---|
|  | Source | GenBank Accession # |JX627336.1|: 5726-7450 Human respiratory syncytial virus strain RSVA/GN435/11, complete genome |
| SEQ ID NO: 19 | 85Mer Template | 5'-GTT GGA AAC TAC ACA CAT CTC CTC TAT GTA CAA CCA ACA CAA AGG AAG GAT CCA ACA TCT GCT TAA CAA GAA CCG ACA GAG GAT G-3' |
| SEQ ID NO: 20 | FWD Primer | 5'-GTT GGA AAC TAC ACA CAT CTC CTC-3' |
| SEQ ID NO: 21 | RWD Primer | 5'-CAT CCT CTG TCG GTT CTT GTT AAG-3' |
| SEQ ID NO: 22 | TaqMan Probe | 5'-/56-FAM/CC AAC ACA AAG GAA GGA TCC AAC ATC TG/3BHQ_1/-3' |

TABLE 4-continued

Respiratory syncytial virus type A sequence information

| SEQ ID NO. | Sequence Information Source | Respiratory syncytial virus type A GenBank Accession # |JX627336.1|: 5726-7450 Human respiratory syncytial virus strain RSVA/GN435/11, complete genome |
|---|---|---|
| SEQ ID NO: 23 | FWD qPrimer | 5'-/5Cy3/GT TGG AAA CTA CAC ACA TCT CCT C-3' |
| SEQ ID NO: 24 | RWD qPrimer | 5'-/5IABkFQ/CA TCC TCT GTC GGT TCT TGT AAA G-3' |

TABLE 5

Respiratory syncytial virus type B sequence information

| SEQ ID NO. | Sequence Information Source | Respiratory syncytial virus type B GenBank Accession # JX682822.1 |
|---|---|---|
| SEQ ID NO: 25 | 81Mer Template | 5'-CCT CAC CTC AAG TCA GAA CAT AAC TGA GGA GTT TTA CCA ATC GAC ATG TAG TGC AGT TAG CAG AGG TTA CTT GAG TGC TTT-3' |
| SEQ ID NO: 26 | FWD Primer | 5'-CCT CAC CTC AAG TCA GAA CAT AAC-3' |
| SEQ ID NO: 27 | RWD Primer | 5'-AAA GCA CTC AAG TAA CCT CTG C-3' |
| SEQ ID NO: 28 | TaqMan Probe | 5'-/56-FAM/AC CAA TCG ACA TGT AGT GCA GT/3BHQ_1/-3' |
| SEQ ID NO: 29 | FWD qPrimer | 5'-/5Cy3/CC TCA CCT CAA GTC AGA ACA TAA C-3' |
| SEQ ID NO: 30 | RWD qPrimer | 5'-/5IABkFQ/AA AGC ACT CAA GTA ACC TCT GC-3' |

TABLE 6

Human rhinovirus sequence information

| SEQ ID NO. | Sequence Information Source | Human rhinovirus GenBank Accession # AF108174.1 |
|---|---|---|
| SEQ ID NO: 31 | 85Mer Template | 5'-ACA ATG GAC AAG GTG TGA AGA GCC CCG TGT GCT CGC TTT GAG TCC TCC GGC CCC TGA ATG TGG CTA ACC TTA ACC TGC AGC TA G-3' |
| SEQ ID NO: 32 | FWD Primer | 5'-ACA ATG GAC AAG GTG TGA AGA G-3' |
| SEQ ID NO: 33 | RWD Primer | 5'-CTA GCT GCA GGG TTA AGG TTA G-3' |
| SEQ ID NO: 34 | TaqMan Probe | 5'-/56-FAM/TG TGC TCG CTT TGA GTC CTC CG/3BHQ_1/-3' |
| SEQ ID NO: 35 | FWD qPrimer | 5'-/5Cy3/AC AAT GGA CAA GGT GTG AAG AG-3' |
| SEQ ID NO: 36 | RWD qPrimer | 5'-/5IABkFQ/CT AGC TGC AGG GTT AAG GTT AG-3' |

TABLE 7

Human metapneumovirus sequence information

| SEQ ID NO. | Sequence Information Source | Human metapneumovirus GenBank Accession # |AF371337.2|: 3052-4671 Human metapneumovirus isolate 00-1, complete genome) |
|---|---|---|
| SEQ ID NO: 37 | 88Mer Template | 5'-GAG AGC ATT GAG AAC AGT CAG GCC TTG GTG GAT CAA TCA AAC AGA ATC TA AGC AGT GCA GAG AAA GGA AAC ACT GGC TTC ATC ATT G-3' |

TABLE 7-continued

Human metapneumovirus sequence information

| SEQ ID NO. | Sequence Information Source | Human metapneumovirus GenBank Accession # |AF371337.2|: 3052-4671 Human metapneumovirus isolate 00-1, complete genome) |
|---|---|---|
| SEQ ID NO: 38 | FWD Primer | 5'-GAG AGC ATT GAG AAC AGT CAG G-3' |
| SEQ ID NO: 39 | RWD Primer | 5'-CAA TGA TGA AGC CAG TGT TTC C-3' |
| SEQ ID NO: 40 | TaqMan Probe | 5'-/56-FAM/AC AGA ATC CTA AGC AGT GCA GAG A/3BHQ_1/-3' |
| SEQ ID NO: 41 | FWD qPrimer | 5'-/5Cy3/GA GAG CAT TGA GAA CAG TCA GG-3' |
| SEQ ID NO: 42 | RWD qPrimer | 5'-/5IABkFQ/CA ATG ATG AAG CCA GTG TTT CC-3' |

TABLE 8

Parainfluenza virus type 3 sequence information

| SEQ ID NO. | Sequence Information Source | Parainfluenza virus type 3 GenBank Accession # gi|403376|emb|Z26523.1| Human parainfluenza virus type 3 HN gene for hemagglutinin-neuraminidase) |
|---|---|---|
| SEQ ID NO: 43 | 86Mer Template | 5'-TCG AGA GTG AAC CCA GTC ATA ACT TAC TCA ACA GCA ACC GAA AGA GTA AAC GAG CTG GCC ATC CGA AAC AGA ACA CTC TCA GCT GG-3' |
| SEQ ID NO: 44 | FWD Primer | 5'-TCG AGA GTG AAC CCA GTC ATA A-3' |
| SEQ ID NO: 45 | RWD Primer | 5'-CCA GCT GAG AGT GTT CTG TTT C-3' |
| SEQ ID NO: 46 | TaqMan Probe 1 | 5'-/56-FAM/CC GAA AGA GTA AAC GAG CTG GCC A/3BHQ_1/-3' |
| SEQ ID NO: 47 | TaqMan Probe 2 | 5'-/5Cy3/CC GAA AGA GTA AAC GAG CTG GCC A/3BHQ_2/-3' |
| SEQ ID NO: 48 | TaqMan Probe 3 | 5'-/56-ROXN/CC GAA AGA GTA AAC GAG CTG GCC A/3BHQ_2/-3' |
| SEQ ID NO: 49 | TaqMan Probe 4 | 5'-/5Cy5/CC GAA AGA GTA AAC GAG CTG GCC A/3IAbRQSp/-3' |

Example 3: Polymerase Chain Reactions

PCR reactions were performed on a Roche 480 LightCycler instrument (Roche Applied Science, Penzberg, Germany). The PCR cycling reaction was run for 45 cycles, with a 60 sec hot-start at 95° C. The cycling conditions were: denaturation for 45 sec at 95° C., annealing for 120 sec at 45° C., and extension for 120 sec at 58° C. Each experiment was run in sextuplicate, with a reaction volume of 15 µL. Fluorescence measurements in 523 nm-568 nm (Cy3) and 615 nm-670 nm (Cy5) were taken at the end of annealing for every cycle. The change in fluorescence intensity between the first and last measurements (the quenched signal) was measured for each experiment.

Positive control experiments were performed to determine base-line quenching levels for each analyte and set of primers. Only analytes with their associated probes were cycled in experiments 1-10, and tabulated in Tables 9-18.

In each experiment, the uncertainty in the cycling data was determined by the spread of values in the last five cycles of the particular amplification reaction. This uncertainty did not scale with the value of the total signal, which implied that the source of uncertainty was instrumental rather than experimental. A 1× fluorophore (200 nM) baseline was determined by statistical analysis of a set of data on 200 nM concentration. The expected multiplicative signal levels were determined by multiplying this baseline by the multiplicity. The change in fluorescence intensity was used to assemble the expected signal levels in the chromatograms depicted in FIGS. 5-9.

Example 4: Detection of HIV TPP Analytes

Figure 7A:
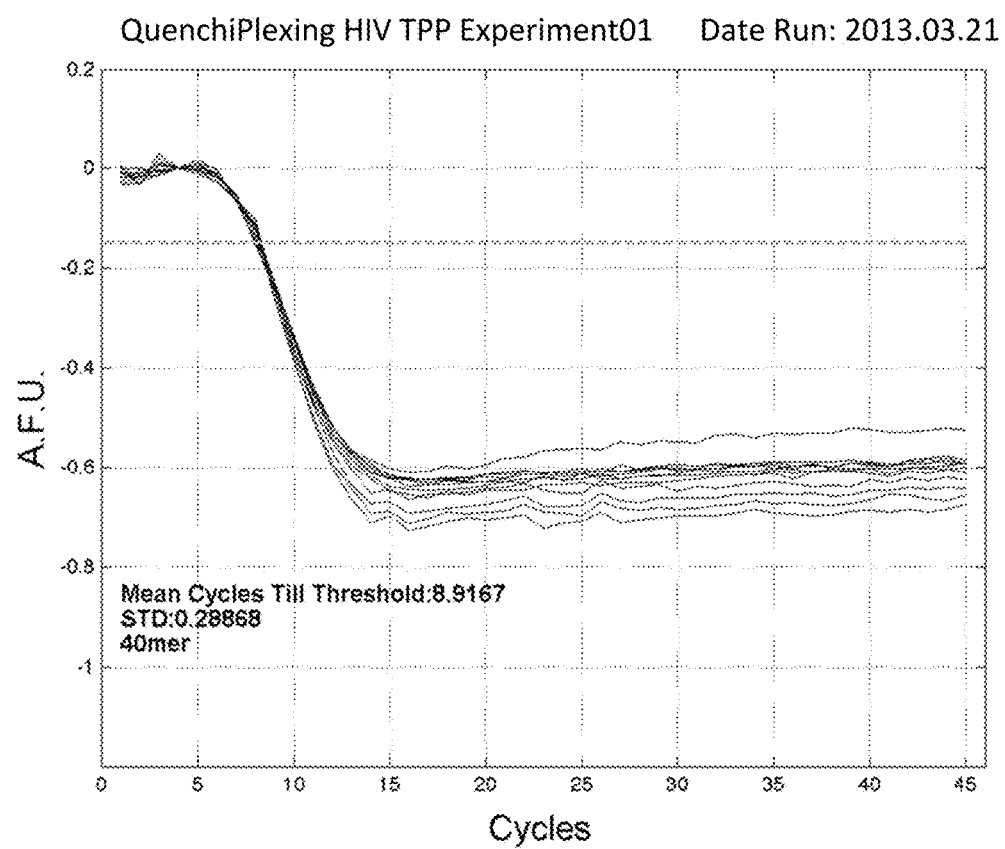
FIG. 7A-FIG. 7C show that the extent of signal generation (quenching) is strongly correlated with the distance between a quencher and a fluorophore. Analytes were varied in length from 40 bp to 120 bp for a single set of primers.
Figure 7B:
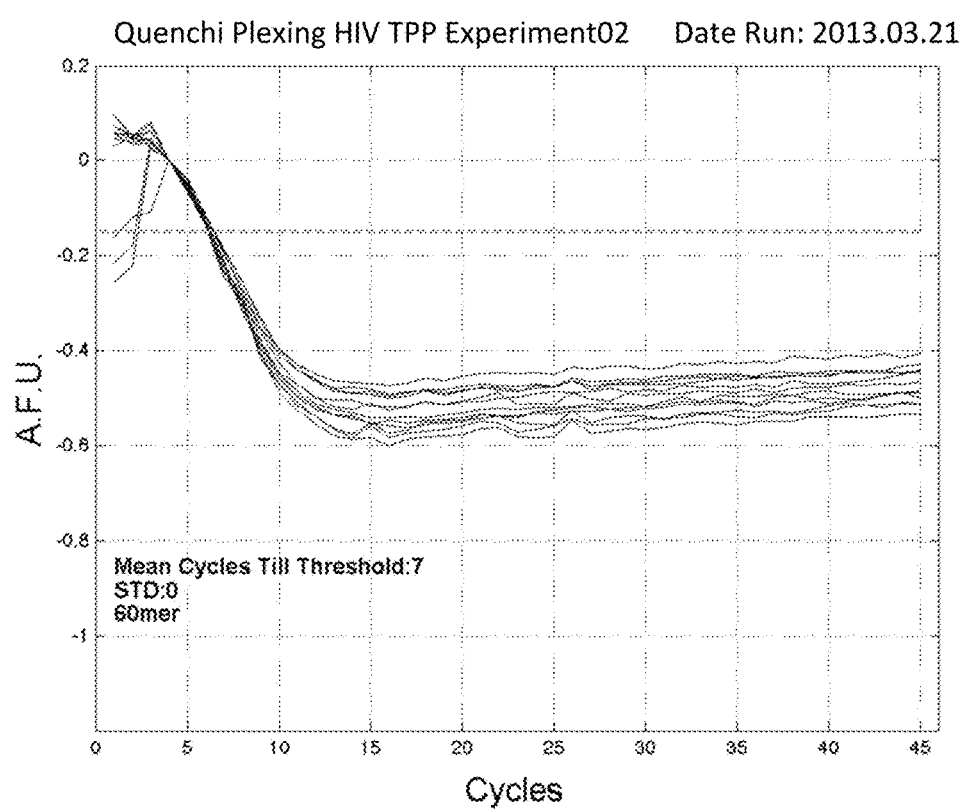
Figure 7C:
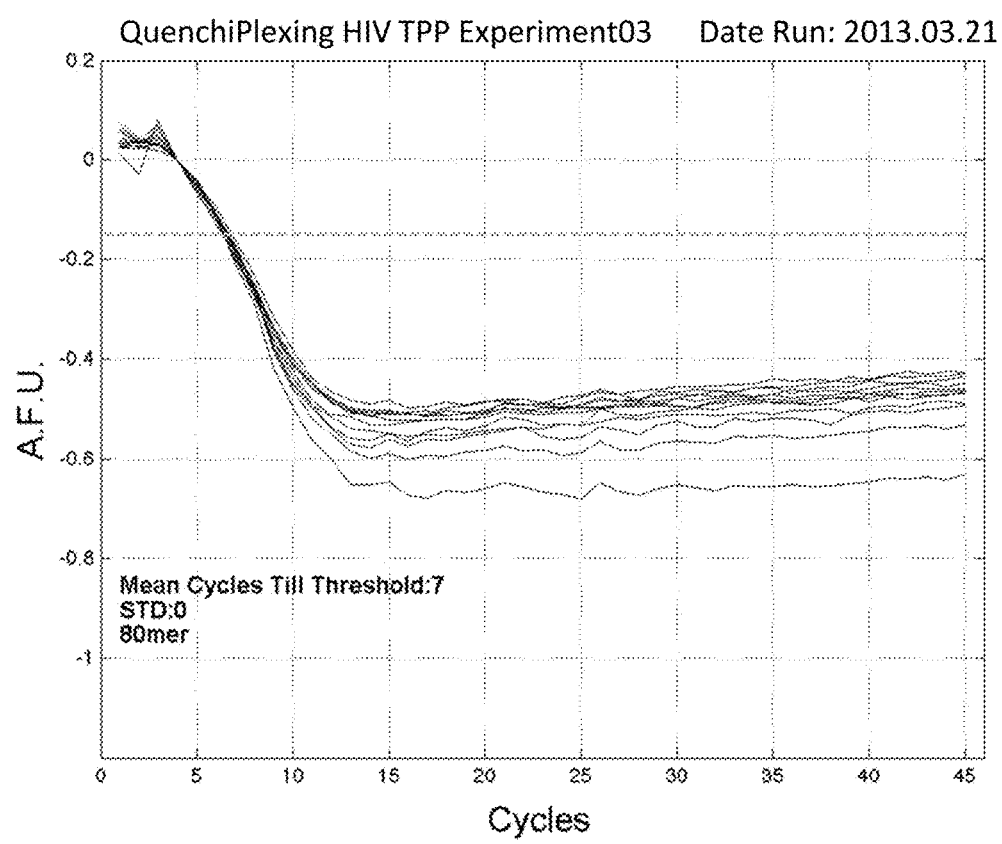

FIG. 5 illustrates the successful detection of HIV TPP analytes using the analytes, primers and methods described in Examples 1-3. Initial experiments showed the quantitative PCR (qPCR) detection of 80 bp HIV TPP analytes at varying concentrations from 10 nM to 10 pM (A-D). All successful detection curves exhibited the inverse-sigmoidal characteristic. FIG. 6 indicates the detection assay can be used to detect low concentrations of HIV TPP. The experiments demonstrated the detection assay was able to detect between 1 pM and 100 fM (FIG. 6A and FIG. 6B) of HIV TPP. FIG. 7 illustrates the length dependence of quenching. Experiments showed that the extent of quenching is strongly correlated to the separation length between a quencher and a fluorophore (FIG. 7A-7C). Analytes were varied in length from 40 bp to 120 bp for a single set of primers.

Example 5: Detection of Single Nucleotide Polymorphisms

Figure 8A:
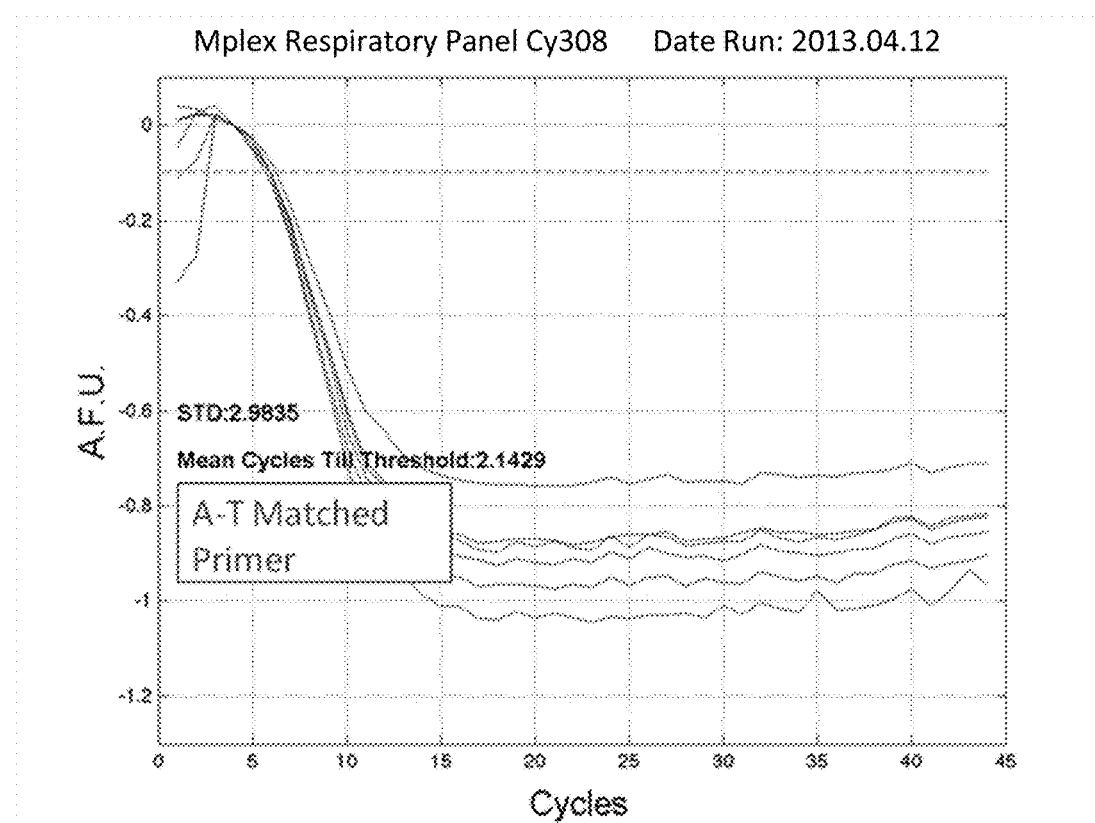
FIG. 8A-FIG. 8B illustrate the effect of a single nucleotide polymorphism on signal generation. Signal level changes significantly when a mis-priming event occurs (FIG. 8A and FIG. 8B).
Figure 8B:
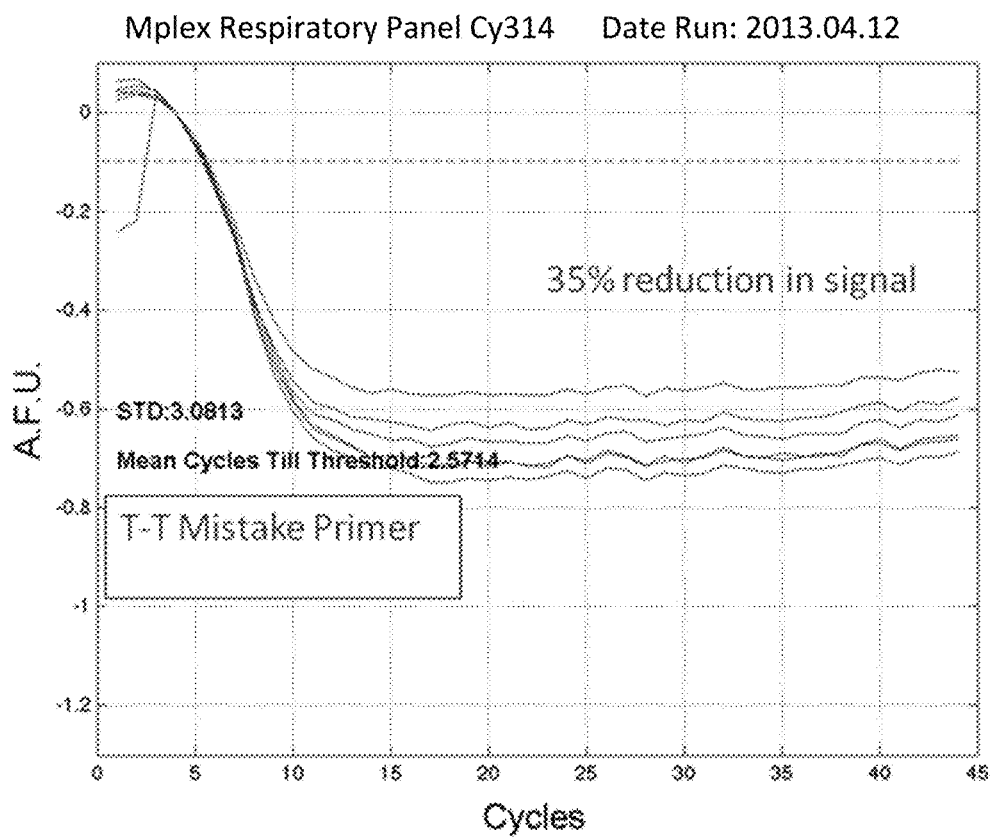

FIG. 8 illustrates the detection of a single nucleotide polymorphism. Signal level changed significantly (approximately a 35% reduction in signal) when a mis-priming event occurred (FIG. 8A and FIG. 8B). The observed effect suggests the mechanism of signal change involved the electron transport between chromophores of the labeled analyte.

Example 6: Multiplex Detection Using Binary Coding of Analytes

FIG. 9 illustrates the binary coding of the analytes. Analytes in a 3-plex CY3 assay were coded using binary spaced primer concentrations. A TaqMan positive control sequence was amplified in every reaction to confirm that the PCR completed successfully.

Example 7: Tagged Primer PCR

This example describes a method of directly detecting a DNA analyte in a sample by incorporating chromophores onto primers and performing a PCR reaction. This method directly detects a PCR product, and does not require a secondary detection technique, such as a gel electrophoresis. For instance, an exemplary analyte is illustrated in FIG. 10A (SEQ ID NO: 50). A forward (FWD) (SEQ ID NO: 51) and reverse or rewind (RWD) (SEQ ID NO: 52) primers are designed such that a quencher and fluorophore are ligated to the 5' of each primer, respectively (FIG. 10B). The primers are selected in appropriate concentrations to limit unbound quenching. Before the first cycle of the PCR reaction is run, the total fluorescence intensity is 10. During the first cycle of the PCR, this intensity level is typically unchanged, as there is no DNA analyte present that incorporates both a fluorophore and a quencher (FIG. 10C; SEQ ID NO: 50-SEQ ID NO: 52). A decrease in signal is observed upon completion of a second PCR cycle (FIGS. 10D and 10E; SEQ ID NO: 50-SEQ ID NO: 52). As the cycles progress, on average, the total fluorescent signal decreases by a factor of 2 per cycle. Therefore, the fluorescent intensity at the end of cycle two is approximately 10/2 because the fluorophore on the anti-sense strand is quenched by the quencher on the sense strand. This attenuation of the fluorescent signal continues until the supply of primers for that analyte is exhausted. In this way, a "dark-field" measurement for the DNA analyte is obtained by looking at the intensity of fluorescence after each cycle.

Example 8: Multiplex Detection Using Various Chromophore Combinations

Figure 11:
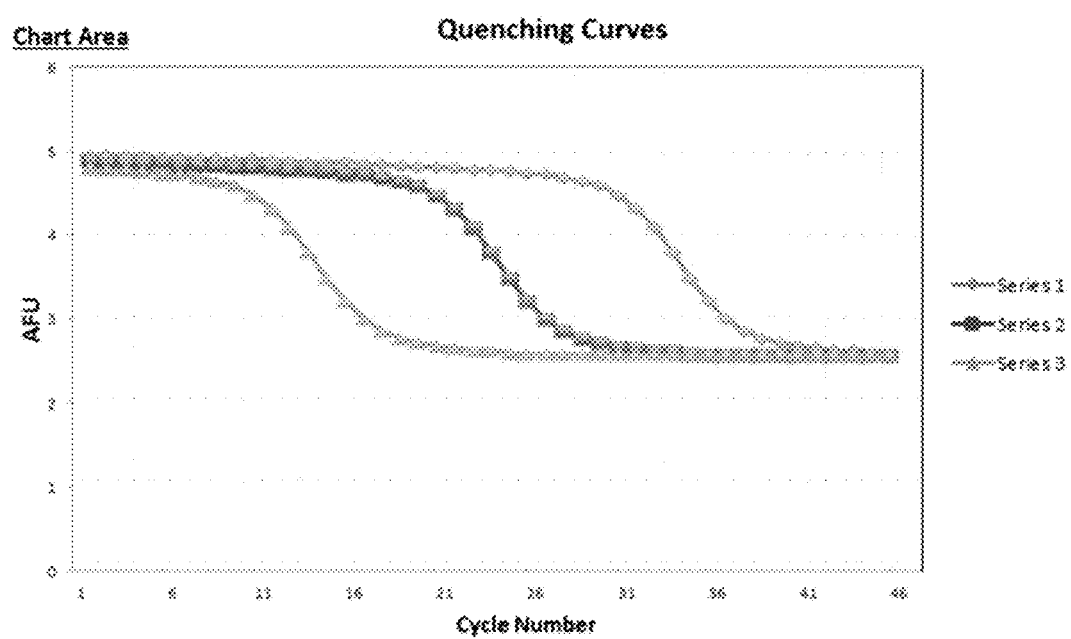
FIG. 11 exemplifies how a detection method described herein can be used in a multiplex reaction to detect quenched signals in three channels.
Figure 13A:
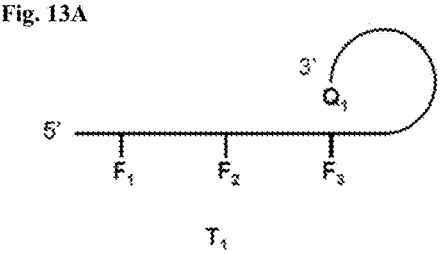
FIG. 13A-FIG. 13D exemplify signal generation as a function of temperature for an analyte containing multiple chromophores.
Figure 13C:
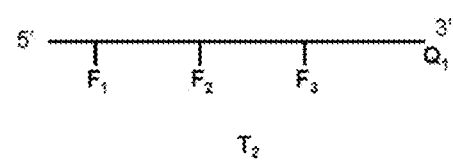
Figure 13B:
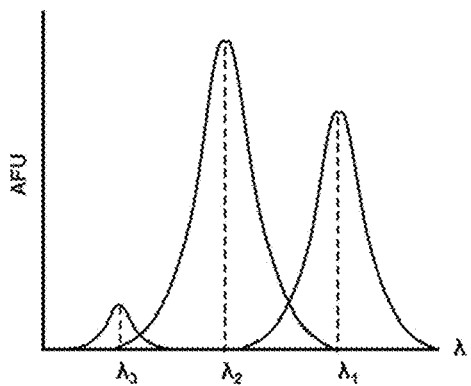
Figure 13D:
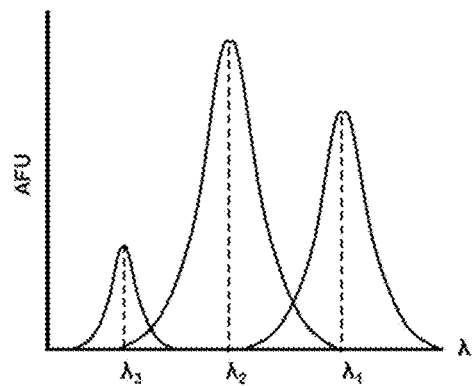

This example describes a technique for distinguishing multiple DNA analytes in a single PCR reaction using various chromophore combinations for each pair of analyte-specific primers. Color multiplexing different strands as illustrated in FIG. 11 is used to distinguish between multiple analytes. Dark-field curves are generated after performing PCR. From these dark-field curves, the initial concentrations are interpolated.

Example 9: Multiplex Detection Using a Single Chromophore Combination

This example describes a technique for distinguishing multiple DNA analytes of varying lengths in a single PCR reaction using the same chromophore combination for each pair of analyte-specific primers. Analytes of differing lengths (e.g., 40 bp, 60 bp, and 80 bp) are detected using a single fluorophore/quencher combination. Longer analytes have a greater separation between the quencher and the fluorophore, and thus exhibit different end point fluorescence levels. In superposition, different combinations of analytes code for different fluorescence levels. Further discrimination of nucleic acid analytes is performed using a melt curve analysis. Lower molecular weight analytes denature at lower temperatures. By measuring fluorescence as a function of increasing temperature, multiple analytes in a single color channel are quantified.

Example 10: Detection of Morphology

This example describes the characterization of the morphology of an analyte (e.g., a DNA analyte) using multiple chromophores. The DNA analyte illustrated in FIG. 12 (SEQ ID NO: 50) has a particular morphology at a given temperature. This morphology results in a fluorescence signature. Changing the temperature results in a different morphology of the DNA analyte, which in turn results in a different fluorescence signature (FIG. 13). The signatures for the morphology of analytes (such as the DNA molecule shown in FIG. 12) are obtained by ramping of the temperature and determining fluorescent signatures. By superimposing these signatures, a three dimensional folding model for the DNA molecule is obtained.

While preferred disclosures of the present disclosure have been shown and described herein, it will be obvious to those skilled in the art that such disclosures are provided by way of example only. Numerous variations, changes, and substitutions will now occur to those skilled in the art without departing from the present disclosure. It should be understood that various alternatives to the disclosures described herein may be employed in practicing the invention. It is intended that the following claims define the scope of the invention and that methods and structures within the scope of these claims and their equivalents be covered thereby.

TABLE 9

Experiment 01 Cocktail

| Reagents | Concentration | Volume Added |
|---|---|---|
| UltraPure H$_2$O | — | 70 μL |
| Taq 5x Master Mix Templates | — | 25 μL |
| Poly Protease 40mer Primers | 12 nM | 5 μL |
| Poly Protease FWD qPrimer | 1 μM | 5 μL |
| Poly Protease RWD qPrimer | 1 μM | 5 μL |

TABLE 10

Experiment 02 Cocktail

| Reagents | Concentration | Volume Added |
|---|---|---|
| UltraPure H$_2$O | — | 70 μL |
| Taq 5x Master Mix | — | 25 μL |

TABLE 10-continued

| Experiment 02 Cocktail | | |
|---|---|---|
| | Concentration | Volume Added |
| Templates | | |
| Poly Protease 60mer | 10 nM | 5 μL |
| Primers | | |
| Poly Protease FWD qPrimer | 1 μM | 5 μL |
| Poly Protease RWD qPrimer | 1 μM | 5 μL |

TABLE 11

| Experiment 03 Cocktail | | |
|---|---|---|
| | Concentration | Volume Added |
| Reagents | | |
| UltraPure $H_2O$ | — | 70 μL |
| Taq 5x Master Mix | — | 25 μL |
| Templates | | |
| Poly Protease 80mer | 10 nM | 5 μL |
| Primers | | |
| Poly Protease FWD qPrimer | 1 μM | 5 μL |
| Poly Protease RWD qPrimer | 1 μM | 5 μL |

TABLE 12

| Experiment 04 Cocktail | | |
|---|---|---|
| | Concentration | Volume Added |
| Reagents | | |
| UltraPure $H_2O$ | — | 70 μL |
| Taq 5x Master Mix | — | 25 μL |
| Templates | | |
| Poly Protease 45mer | 10 nM | 5 μL |
| Primers | | |
| Poly Protease FWD qPrimer | 1 μM | 5 μL |
| Poly Protease RWD qPrimer | 1 μM | 5 μL |

TABLE 13

| Experiment 05 Cocktail | | |
|---|---|---|
| | Concentration | Volume Added |
| Reagents | | |
| UltraPure $H_2O$ | — | 70 μL |
| Taq 5x Master Mix | — | 25 μL |
| Templates | | |
| Poly Protease 50mer | 10 nM | 5 μL |
| Primers | | |
| Poly Protease FWD qPrimer | 1 μM | 5 μL |
| Poly Protease RWD qPrimer | 1 μM | 5 μL |

TABLE 14

| Experiment 06 Cocktail | | |
|---|---|---|
| | Concentration | Volume Added |
| Reagents | | |
| UltraPure $H_2O$ | — | 70 μL |
| Taq 5x Master Mix | — | 25 μL |
| Templates | | |
| Poly Protease 55mer | 10 nM | 5 μL |
| Primers | | |
| Poly Protease FWD qPrimer | 1 μM | 5 μL |
| Poly Protease RWD qPrimer | 1 μM | 5 μL |

TABLE 15

| Experiment 07 Cocktail | | |
|---|---|---|
| | Concentration | Volume Added |
| Reagents | | |
| UltraPure $H_2O$ | — | 70 μL |
| Taq 5x Master Mix | — | 25 μL |
| Templates | | |
| Poly Protease 100mer | 10 nM | 5 μL |
| Primers | | |
| Poly Protease FWD qPrimer | 1 μM | 5 μL |
| Poly Protease RWD qPrimer | 1 μM | 5 μL |

TABLE 16

| Experiment 08 Cocktail | | |
|---|---|---|
| | Concentration | Volume Added |
| Reagents | | |
| UltraPure $H_2O$ | — | 70 μL |
| Taq 5x Master Mix | — | 25 μL |
| Templates | | |
| Poly Protease 120mer | 10 nM | 5 μL |
| Primers | | |
| Poly Protease FWD qPrimer | 1 μM | 5 μL |
| Poly Protease RWD qPrimer | 1 μM | 5 μL |

TABLE 17

| Experiment 09 Cocktail | | |
|---|---|---|
| | Concentration | Volume Added |
| Reagents | | |
| UltraPure $H_2O$ | — | 105 μL |
| Taq 5x Master Mix | — | 75 μL |
| Templates | | |
| Influenza A 85mer | 10 nM | 5 μL |
| Primers | | |
| Influenza A FWD qPrimer | 300 nM | 5 μL |
| Influenza A RWD qPrimer | 300 nM | 5 μL |

TABLE 18

Experiment 10 Cocktail

| Reagents | Concentration | Volume Added |
|---|---|---|
| UltraPure H$_2$O | — | 105 μL |
| Taq 5x Master Mix | — | 75 μL |
| Templates | | |
| Influenza B 81mer | 10 nM | 5 μL |

TABLE 18-continued

Experiment 10 Cocktail

| | Concentration | Volume Added |
|---|---|---|
| Primers | | |
| Influenza B FWD qPrimer | 300 nM | 5 μL |
| Influenza B RWD qPrimer | 300 nM | 5 μL |

What is claimed is:

1. A method of detecting at least one genetic variation in a polynucleotide analyte in a sample, comprising:
   a) combining the sample comprising the polynucleotide analyte with a first primer and a second primer, wherein a fluorophore is attached to the first primer, a quencher is attached to the second primer, the first primer and the second primer are specific for the first polynucleotide analyte, at least one of the first primer and the second primer hybridizes to a region of the polynucleotide analyte encoding the at least one genetic variation, and the fluorophore is different from the quencher;
   b) measuring a first signal generated by the fluorophore and quencher;
   c) performing at least one polymerase chain reaction (PCR) reaction with the first primer and the second primer using the polynucleotide analyte as a template, thereby amplifying the template to generate a PCR amplification product comprising the at least one genetic variation;
   d) measuring a second signal generated by the fluorophore and quencher from the PCR amplification product;
   e) comparing the first and second signals to determine a change between the first and second signals; and
   f) determining the presence or absence of the at least one genetic variation based i) on the change in signal as determined in step e); and ii) by comparing said change to the change in signal observed upon PCR amplification for a corresponding polynucleotide analyte lacking the at least one genetic variation in the presence of the first primer and the second primer.

2. The method of claim 1, wherein the at least one genetic variation is present when the change in signal as determined in step e) is a decrease in change when compared to the change in signal observed for the corresponding polynucleotide analyte lacking the at least one genetic variation.

3. The method of claim 1, wherein the genetic variation comprises a single-nucleotide polymorphism (SNP).

4. The method of claim 3, wherein the first primer hybridizes to a region of the polynucleotide analyte encoding the SNP.

5. The method of claim 3, wherein the second primer hybridizes to a region of the polynucleotide analyte encoding the SNP.

6. The method of claim 1, wherein the change in signal as determined in step e) is distinct for UU, UT, UG, UC, UA, AA, TT, GG, CC, AG, AC, TG, and TC.

7. The method of claim 1, wherein the fluorophore is attached to the 5' end of the first primer.

8. The method of claim 1, wherein the fluorophore is 6-FAM (Fluorescein), 6-FAM (NHS Ester), Fluorescein dT, HEX, JOE (NHS Ester), MAX, TET, ROX, TAMRA, TARMA (NHS Ester), TEX 615, ATTO 488, ATTO 532, ATTO 550, ATTO 565, ATTO Rho101, ATTO 590, ATTO 633, ATTO 647N, TYE 563, TYE 665 or TYE 705.

9. The method of claim 1, wherein the quencher is attached to the 5' end of the second primer.

10. The method of claim 1, wherein the quencher is Iowa Black FG, Iowa Black RG, BHQ1, BHQ2 or BHQ3.

11. The method of claim 1, wherein the decrease in fluorescent intensity is at least, or about, a 30% decrease in signal.

12. The method of claim 1, wherein the PCR reaction is an end-point polymerase chain reaction process, a real-time polymerase chain reaction process, a digital polymerase chain reaction process, a droplet digital polymerase chain reaction process, or a quantitative polymerase chain reaction process.

13. The method of claim 1, wherein the PCR reaction is a quantitative PCR process.

14. The method of claim 1, wherein the concentration of the polynucleotide analyte is from about 10 µM to about 10 aM.

15. The method of claim 1, wherein the polynucleotide analyte is a DNA polynucleotide analyte or an RNA polynucleotide analyte.

16. The method of claim 1, further comprising detecting at least one additional polynucleotide analyte within the sample with an additional fluorophore attached to a primer, wherein the fluorophore is the same color as the additional fluorophore.

17. The method of claim 1, wherein the polynucleotide analyte is from about 10 to about 500 nucleotides in length.

18. The method of claim 1, wherein the first primer encodes a region on the analyte less than 500 base pairs away from a region encoded by the second primer.

19. The method of claim 3, wherein the SNP is associated with a disease, optionally a genetic disorder, an autoimmune disease, a neurological disease, a cardiovascular disease, or a cancer.

20. The method of claim 1, wherein when the first primer is hybridized to the region of the polynucleotide analyte encoding the at least one genetic variation, the fluorophore is attached to a portion of the first primer that is 5' to the site of the at least one genetic variation.

21. The method of claim 1, wherein when the second primer is hybridized to the region of the polynucleotide analyte encoding the at least one genetic variation, the quencher is attached to a portion of the second primer that is 5' to the site of the at least one genetic variation.

22. The method of claim 1, wherein the genetic variation comprises a deletion, an insertion, a point mutation, a base-pair substitution, or a variation in the number of multiple nucleotide repetition.

23. The method of claim 1, wherein the corresponding polynucleotide analyte is a wild-type analyte.

* * * * *